US010190177B2

(12) United States Patent
Mustapha et al.

(10) Patent No.: US 10,190,177 B2
(45) Date of Patent: Jan. 29, 2019

(54) MULTIPLEX ASSAY FOR DETECTION OF BACTERIAL SPECIES IN BIOLOGICAL SAMPLES

(71) Applicants: Azlin Mustapha, Columbia, MO (US); Prashant Singh, Columbia, MO (US)

(72) Inventors: Azlin Mustapha, Columbia, MO (US); Prashant Singh, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 534 days.

(21) Appl. No.: 14/810,242

(22) Filed: Jul. 27, 2015

(65) Prior Publication Data
US 2016/0032366 A1 Feb. 4, 2016

Related U.S. Application Data

(60) Provisional application No. 61/999,642, filed on Aug. 1, 2014.

(51) Int. Cl.
C12Q 1/689 (2018.01)
(52) U.S. Cl.
CPC ....... C12Q 1/689 (2013.01); C12Q 2600/158 (2013.01); C12Q 2600/16 (2013.01)
(58) Field of Classification Search
None
See application file for complete search history.

(56) References Cited

U.S. PATENT DOCUMENTS

2004/0072239 A1* 4/2004 Renaud ........... C12Q 1/689 435/7.1
2013/0078634 A1* 3/2013 Varkey ........... C12Q 1/689 435/6.11

OTHER PUBLICATIONS

Dymond, J.S. Methods in Enzymology 2013; 529: 279-289. (Year: 2013).*
Takeshi et al. Microbiology and Immunology 1997; 41: 819-822. (Year: 1997).*
Ogden et al. Journal of Applied Microbiology 2001; 91: 373-379. (Year: 2001).*
Anklam et al., "Rapid and reliable detection of Shiga toxin-producing Escherichia coli by real-time multiplex PCR," J Food Protect, 75:643-650, 2012.
Bai et al., Applicability of a multiplex PCR to detect the seven major Shiga toxin-producing Escherichia coli based on genes that code for Serogroup-Specific O-Antigens and major virulence factors in cattle feces, Foodborne Pathog Dis, 9:541-548, 2012.
Baranzoni et al., "Detection and isolation of Shiga toxin-producing Escherichia coli (STEC) O104 from sprouts," Int J Food Microbiol, 173:99-104, 2014.
Baylis, "Growth of pure cultures of Verocytotoxin producing Escherichia coli in a range of enrichment media," J Appl Microbiol, 105(5):1259-1265, 2008.
Bush et al., "Updated functional classification of beta-lactamases," Antimicrob Agents Chemother, 54:969-976, 2010.
Cantón et al., "Rapid evolution and spread of carbapenemases among Enterobacteriaceae in Europe," Clin Microbiol Infect, 18:413-431, 2012.
Cebula et al., "Simultaneous identification of strains of Escherichia coli serotype O157:H7 and their Shiga-like toxin type by mismatch amplification mutation assay-multiplex PCR," J Clin Microbiol, 33:248-250, 1995.
Chassagne et al., "Detection of stx1, stx2, and eae genes of enterohemorrhagic Escherichia coli using SYBR Green in a real-time polymerase chain reaction," Diagn Microbiol Infect Dis, 649:98-101, 2009.
Dewsbury et al., "Summer and Winter Prevalence of Shiga Toxin-Producing Escherichia coli (STEC) O26, O45, O103, O111, O121, O145, and O157 in Feces of Feedlot Cattle," Foodborne Pathog Dis, 12:726-732, 2015.
Feng, "Identification of Escherichia coil serotype O157: H7 by DNA probe specific for an allele of uidA gene," Mol Cell Probes, 7:151-154, 1993.
Feng et al, "Specificity of PCR and Serological Assays in the Detection of Escherichia coli Shiga Toxin Subtypes," Appl Environ Microbiol, 77:6699-6702, 2011.
Folster et al., "Characterization of extended-spectrum cephalosporin-resistant Salmonella enterica serovar Heidelberg isolated from food animals, retail meat, and humans in the United States 2009," Foodborne Pathog Dis, 9:638-645, 2012.
Fratamico et al., "Detection by multiplex real-time polymerase chain reaction assays and isolation of Shiga toxin-producing Escherichia coli Serogroups O26, O45, O103, O111, O121, and O145 in ground beef," Foodborne Pathog Dis, 8:601-607, 2011.
Fratamico et al., "Evaluation of a multiplex real-time PCR method for detecting Shiga toxin-producing Escherichia coli in beef and comparison to the US Department of Agriculture food Safety and Inspection Service Microbiology Laboratory Guidebook method," J Food Protect, 77(2):180-188. 2014.
Hofko et al., "Detection of carbapenemases by real-time PCR and melt curve analysis on the BD Max system," J Clin Microbiol, 52:1701-1704, 2014.
Kanki et al., "Comparison of four enrichment broths for the detection of non-O157 Shiga-toxin producing Escherichia coli O91, O103, O111, O119, O121, O145 and O165 from pure culture and food samples," Lett Appl Microbiol, 53:167-173, 2011.
Lin et al., "O serogroup specific real time PCR assays for the detection and identification of nine clinically relevant non-O157 STECs," Food Microbiol, 28:478-483, 2011.
Lupo et al., "Non-phenotypic tests to detect and characterize antibiotic resistance mechanisms in Enterobacteriac," Diagn Microbiol Infect Dis, 77:179-194, 2013.
Malorny et al., "Multicenter validation study of two blockcycler- and one capillary-based real-time PCR methods for the detection of Salmonella in milk powder," Int J Food Microbiol, 117:211-218, 2007.

(Continued)

Primary Examiner — Angela M. Bertagna
(74) Attorney, Agent, or Firm — Dentons US LLP

(57) ABSTRACT

The invention provides a rapid, accurate, sensitive, and low-cost detection method for screening a biological sample for one or more desired bacterial species. The inventive method employs a two-step multiplex real-time PCR assay that comprises an internal amplification control and specific primer sets to detect and discriminate bacterial species based the unique melting temperatures of specific DNA sequences of each strain.

28 Claims, 7 Drawing Sheets

Specification includes a Sequence Listing.

(56) References Cited

OTHER PUBLICATIONS

Margot et al., "Evaluation of seven different commercially available real-time PCR assays for detection of shiga toxin 1 and 2 gene subtypes," *J Food Prot*, 76:871-873, 2013.

Monteiro et al., "Rapid detection of carbapenemase genes by multiplex real-time PCR," *J Antimicrob Chemother*, 67:906-909, 2012.

Naas et al., "Real-Time PCR for Detection of NDM-1 Carbapenemase Genes from Spiked Stool Samples," *Antimicrob Agents Chemother*, 55:4038-4043, 2011.

Nordmann et al., "Global Spread of Carbapenemase-producing Enterobacteriaceae," *Emerg Infect Dis*, 17:1791-1798, 2011.

Paton et al., Molecular characterization of the locus encoding biosynthesis of the lipopolysaccharide O antigen of *Escherichia coli* serotype O113, *Infect Immun*, 67:5930-5937, 1999.

Persson et al., "Subtyping method of *Escherichia coli* Shiga toxin (verocytotoxin) 2 variants and correlations to clinical manifestations," *J Clin Microbiol*, 45:2020-2024, 2007.

Queenan et al., "Carbapenemases: the Versatile β-Lactamases," *Clin Microbiol Rev*, 20:440-458, 2007.

Rahn et al., "Amplification of an invA gene sequence of *Salmonella typhimurium* by polymerase chain reaction as a specific method of detection of *Salmonella*," *Mol Cell Probes*, 6:271-279, 1992.

Singh et al., "Rectal screening for *Klebsiella pneumoniae* carbapenemases: Comparison of real-time PCR and culture using two selective screening agar plat," *J Clin Microbiol*, 50:2596-2600, 2012.

Wang et al., "Detection of viable *Escherichia coil* O157: H7 by ethidium monoazide real-time PCR," *J Appl Microbiol*, 107:1719-1728, 2009.

Mathew et al., "Antibiotic Resistance in Bacteria Associated with Food Animals: A United States Perspective of Livestock Production," *Foodborne Pathog Dis*, 4:115-133, 2007.

Monday et al., "Identification of Shiga toxingenic *Escherichia coli* seropathotypes A and B by multiplex PCR," *Mol Cell Probes*, 21:308-311, 2007.

Singh et al., "Detection of Shiga toxin-producing *Escherichia coli*, seven stx subtypes and *Salmonella* via a two-tiered multiplex real-time PCR," International Association of Food Protection, 2015.

Singh et al., "Multiplex Real-time PCR Asay for Detection of Eight STEC Serotypes," International Association for Food Protection, 2014.

Singh et al., "Development of a real-time PCR melt curve assay for simultaneous detection of virulent and antibiotic resistant *Salmonella*," *Food Microbiol*, 44:6-14, 2014.

Sjölund-Karlsson et al., "Occurrence of β-lactamase genes among non-Typhi *Salmonella enterica* isolated from humans, food animals, and retail meats in the United States and Canada," *Microb Drug Resist*, 19:191-197, 2013.

Smet et al., "Broad-spectrum β-lactamases among Enterobacteriaceae of animal origin: molecular aspects, mobility and impact on public health," *FEMS Microbiol Rev*, 34:295-316, 2010.

Smith et al., "Shiga toxin-producing *Escherichia coli*," *Adv Appl Microbiol*, 86:145-197, 2014.

Stromberg et al., "Prevalence of enterohemorrhagic *Escherichia coli* O26, O45, O103, O111, O121, O145, and O157 on hides and preintervention carcass surfaces of feedlot cattle at harvest," *Foodborne Pathog Dis*, 12:631-638, 2015.

Valadez et al., "Multiplex PCR detection of Shiga toxin-producing *Escherichia coli* strains belonging to serogroups O157, O103, O91, O113, O145, O111, and O26 experimentally inoculated in beef carcass swabs, beef trim, and ground beef," *J Food Prot*, 74:228-239, 2011.

Vogne et al., "A simple, robust and rapid approach to detect carbapenemases in Gram-negative isolates by MALDI-TOF mass spectrometry: Validation with triple quadripole tandem mass spectrometry, microarray and PCR," *Clin Microbiol Infect*, 20:O1106-O1112, 2014.

Wang et al., "Rapid and specific detection of *Escherichia coli* serogroups O26, O45, O103, O111, O121, O145, and O157 in ground beef, beef trim, and produce by loop-mediated isothermal amplification" *Appl Environ Microbiol*, 78:2727-2736, 2007.

Wang et al., "Detection of viable *Escherichia coli* O157: H7 by ethidium monoazide real-time PCR," *J Appl Microbiol*, 107:1719-1728, 2009.

Weagant et al., "Evaluation of techniques for enrichment and isolation of *Escherichia coli* O157: H7 from artificially contaminated sprouts," *J Food Microbiol*, 71:87-92, 2001.

Zhao et al., "Epidemiology and genetics of CTX-M extended-spectrum β-lactamases in Gram-negative bacteria," *Crit Rev Microbiol*, 39:79-101, 2013.

\* cited by examiner

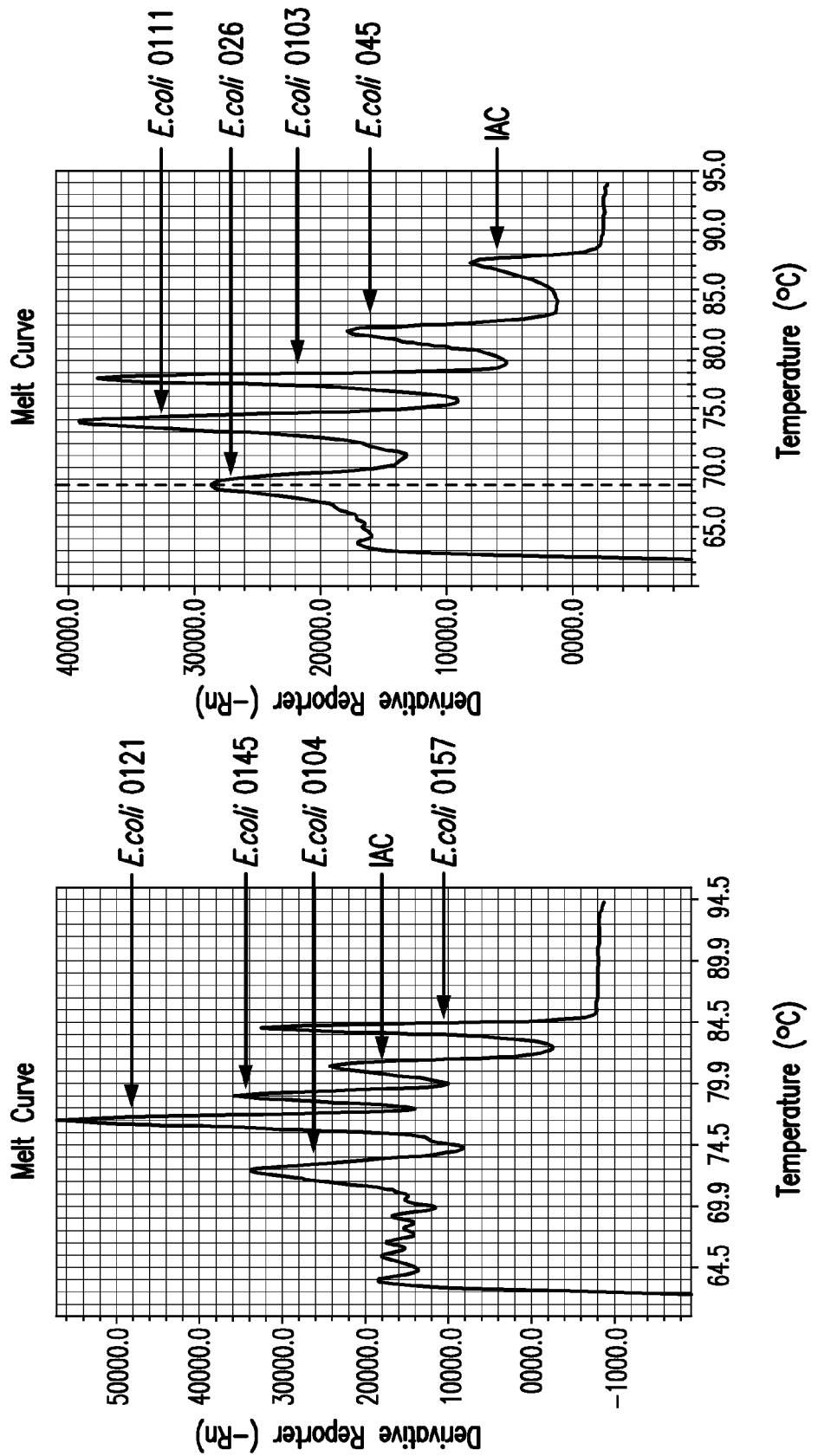

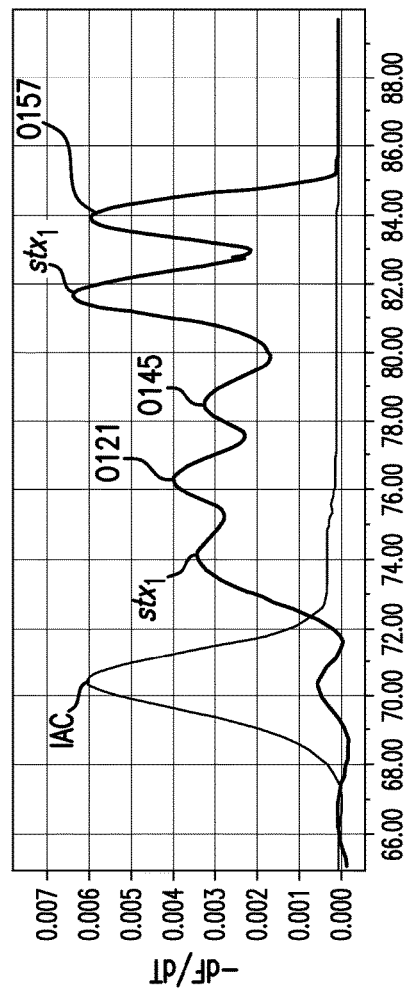 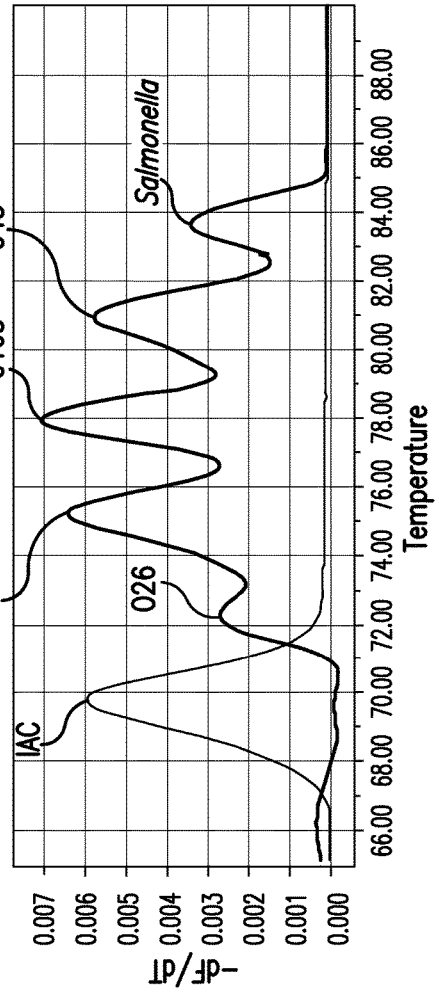
FIG. 4A
FIG. 4B

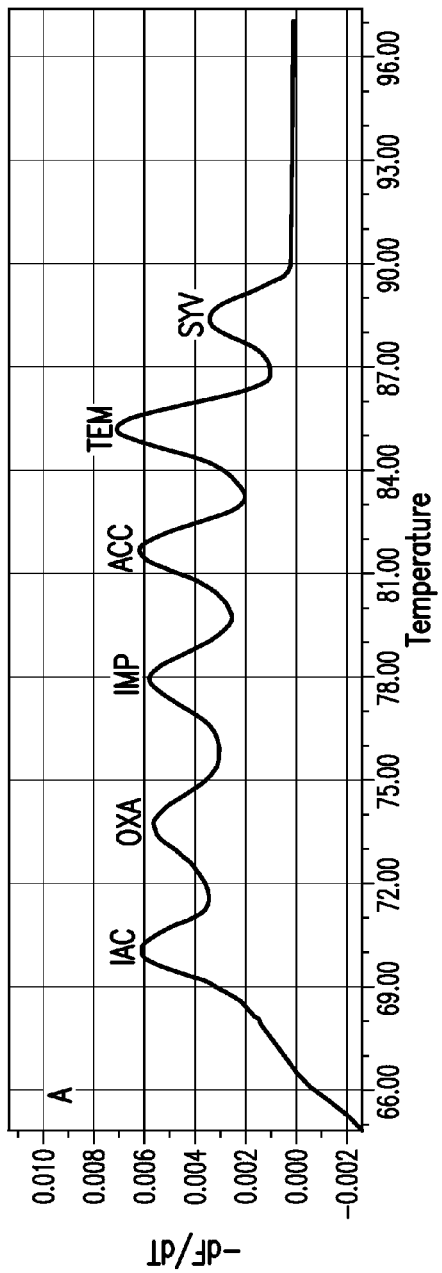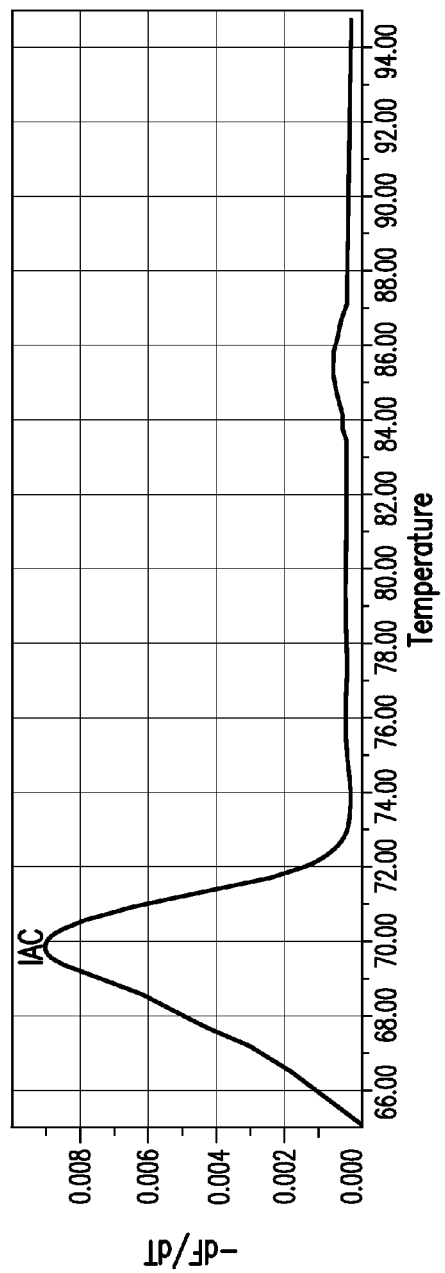
FIG. 6A
FIG. 6B

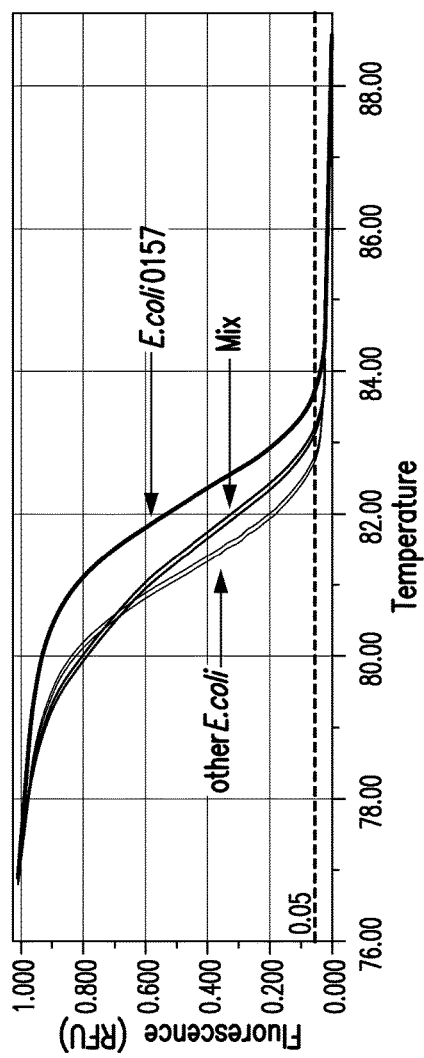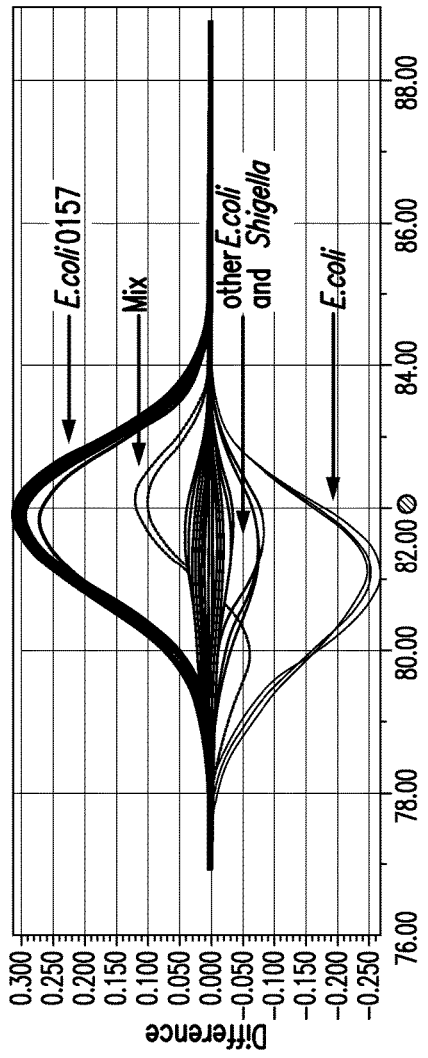

MULTIPLEX ASSAY FOR DETECTION OF BACTERIAL SPECIES IN BIOLOGICAL SAMPLES

CROSS REFERENCE TO RELATED APPLICATIONS

This application claims priority to U.S. Provisional Application No. 61/999,642, filed Aug. 1, 2014, which is herein incorporated by reference in its entirety.

FIELD OF THE INVENTION

The present invention relates to methods for detecting bacterial species in biological samples, more specifically to probe-free methods for detecting multiple bacterial species in food samples.

INCORPORATION OF SEQUENCE LISTING

The sequence listing that is contained in the file named "UVMO114US_ST25" which is 10.7 kilobytes as measured in Microsoft Windows operating system and was created on Jul. 27, 2015, is filed electronically herewith and incorporated herein by reference.

BACKGROUND OF THE INVENTION

There is a current lack of rapid, accurate, and sensitive methods for identifying and detecting virulent or antibiotic resistant bacteria in biological or food samples. Immunological methods such as immunomagnetic separation (IMS) and latex agglutination are rapid and easy to perform for the detection of such bacteria. However, manufacturing kits useful for detection requires high quality antibodies and reagents. Further, commercially available differential agar media used for the isolation of virulent or antibiotic resistant bacteria suffer from their inability to differentiate pathogenic or antibiotic resistant bacteria from non-pathogenic bacteria in mixed bacterial samples. Molecular methods, such as TaqMan™ real-time PCR are specific as well as sensitive methods for the detection of specific species or strains of bacteria, but these methods rely on specific fluorescent probes, which are not only costly but degrade rapidly during long storage. Therefore, new methods are needed for detecting and distinguishing between individual bacterial species.

SUMMARY OF THE INVENTION

In one aspect, the present invention provides a method for detecting Shiga toxin-producing *E. coli* (STEC) in a biological sample comprising the steps of: (i) enriching the bacterial concentration of the biological sample to result in an enriched sample; ii) isolating DNA from said enriched biological sample; and (iii) detecting more than one STEC sequence in said isolated DNA sample via real-time PCR and a melt curve assay. In one embodiment, the real-time PCR comprises more than one primer pair. In another embodiment, the real-time PCR comprises an internal amplification control. In other embodiments, the enriching step comprises incubating the biological sample aerobically at 42° C.±1° C. in an enrichment media, for example from about 6 hours to about 12 hours, or the enrichment media is selected from the group consisting of brain heart infusion broth (BHI), tryptic soy broth (TSB), and Buffered Peptone Water (BPW). In another embodiment, the enrichment media is BPW supplemented with vancomycin. In further embodiments, the more than one primer pair comprises a primer pair producing an amplicon comprising a melting temperature between 67° C. to 87° C., or each amplicon comprises a melting temperature differing by 2-3° C. from other amplicons in the real-time PCR. In some embodiments, the primer pairs are set forth in Tables 2 or 3, or the internal amplification control is set forth in Tables 2 or 3. In another embodiment, the biological sample comprises a food or a beverage, such as meat, produce, or juice. In another embodiment, the biological sample comprises a clinical sample, such as stool, urine, or blood. In still another embodiment, the Shiga toxin-producing *E. coli* are selected from the group consisting of *E. coli* O145, *E. coli* O121, *E. coli* O104, *E. coli* O157, *E. coli* O26, *E. coli* O45, *E. coli* O103, and *E. coli* O111.

In another aspect, the invention provides a method for detection of at least one bacterial species in a biological sample comprising real-time PCR amplification, the method comprising: (i) enriching the bacterial concentration of the biological sample to result in an enriched sample; (ii) isolating DNA from the enriched biological sample; and (iii) detecting a sequence from the at least one bacterial species in the isolated DNA sample via real-time PCR wherein the real-time PCR comprises: (a) an internal amplification control comprising at least 90% identity to the internal amplification control set forth in Table 7 and more than one primer pair comprising at least 90% sequence identity to a primer set forth in Table 7; (b) an internal amplification control comprising at least 90% identity to the internal amplification control set forth in Table 8 and more than one primer pair comprising at least 90% sequence identity to a primer set forth in Table 8; (c) an internal amplification control comprising at least 90% identity to the internal amplification control set forth in Table 10 and more than one primer pair comprising at least 90% sequence identity to a primer set forth in Table 10; (d) an internal amplification control comprising at least 90% identity to the internal amplification control set forth in Table 11 and more than one primer pair comprising at least 90% sequence identity to a primer set forth in Table 11; or (e) a primer pair comprising a first primer molecule comprising at least 90% sequence identity to SEQ ID NO:54 and a second primer molecule comprising at least 90% identity to SEQ ID NO:55. In one embodiment, the real-time PCR comprises: (a) an internal amplification control and more than one primer pair set forth in Table 7; (b) an internal amplification control and more than one primer pair set forth in Table 8; (c) an internal amplification control and more than one primer pair set forth in Table 10; (d) an internal amplification control and more than one primer pair set forth in Table 11; or (e) a primer pair comprising SEQ ID NO:54 and SEQ ID NO:55. In another embodiment, the method further comprises a melt curve assay for visualization of individual amplicons in the biological sample. In another embodiment, detecting the at least one sequence comprises: (1) a first real-time PCR with the more than one primer pair and an internal amplification control of part (a) and a second real-time PCR with the more than one primer pair and an internal amplification control of part (b); or (2) a first real-time PCR with the more than one primer pair and an internal amplification control of part (c) and a second real-time PCR with the more than one primer pair and an internal amplification control of part (d). In other embodiments, the enriching step comprises incubating the biological sample aerobically at approximately 42° C. in an enrichment media, such as brain heart infusion broth (BHI), tryptic soy broth (TSB), and Buffered Peptone Water (BPW), or the enrichment media is supplemented with an antibiotic. In another embodiment, the enrichment media is BPW supplemented with vancomycin. In another embodiment, the biological sample comprises a food or a beverage, such as meat, produce, or juice. In still another embodiment, the biological sample comprises a clinical sample such as stool, urine, or blood. In a further embodiment, the sequence comprises: (1) a sequence from at least one bacterial species selected from the group consisting of $E.\ coli$ O121, $E.\ coli$ O145, $E.\ coli$ O157, $E.\ coli$ O26, $E.\ coli$ O111, $E.\ coli$ O103, $E.\ coli$ O45, and $Salmonella$; or a $stx_1$ or $stx_2$ sequence; (2) a sequence e selected from the group consisting of $bla_{KPC-like}$, $bla_{NDM-like}$, $bla_{CTX-M-1/2group}$, $bla_{CMY-like}$, $bla_{VIM-like}$, $bla_{IMP-like}$, $bla_{OXA-like}$, $bla_{SHV-like}$, $bla_{TEM-like}$, and $bla_{ACC-like}$; or (3) a sequence from $E.\ coli$ O157.

In another aspect, the invention provides a kit for detection of at least one bacterial species in a biological sample, comprising: (i) an internal amplification control and more than one primer pair set forth in Table 2; (ii) an internal amplification control and more than one primer pair set forth in Table 3; (iii) an internal amplification control and more than one primer pair set forth in Table 7; (iv) an internal amplification control and more than one primer pair set forth in Table 8; (v) an internal amplification control and more than one primer pair set forth in Table 10; (vi) an internal amplification control and more than one primer pair set forth in Table 11; or (vii) a primer pair comprising SEQ ID NO:54 and SEQ ID NO:55.

BRIEF DESCRIPTION OF THE DRAWINGS

FIGS. 1A-1B—Shows a melt curve for a multiplex real-time PCR assay for the detection of: $E.\ coli$ O145, $E.\ coli$ O121, $E.\ coli$ O104, and $E.\ coli$ O157, with an internal amplification control (IAC) (FIG. 1A); and $E.\ coli$ O26, $E.\ coli$ O45, $E.\ coli$ O103, and $E.\ coli$ 111, with an IAC (FIG. 1B).

FIG. 2A shows multiplex 1 targeting $E.\ coli$ O145, $E.\ coli$ O121, $E.\ coli$ O104, and $E.\ coli$ O157, with an IAC, with a range of 13.5 ng to 135 pg per 10 µL reaction; and FIG. 2B shown multiplex 2 targeting $E.\ coli$ O26, $E.\ coli$ O45, $E.\ coli$ O103, and $E.\ coli$ 111, with an IAC, with a range of 10.3 ng to 103 pg per 10 µL reaction.

FIGS. 4A-4B—Shows a melt curve for a multiplex real-time PCR assay for the detection of: $stx_1$, $E.\ coli$ O121, $E.\ coli$ O145, $stx_2$, and $E.\ coli$ O157, with an IAC (FIG. 4A); and $E.\ coli$ O26, $E.\ coli$ O111, $E.\ coli$ O103, $E.\ coli$ O45, and $Salmonella$, with an IAC (FIG. 4B).

FIGS. 6A-6B—Shows a melt curve for a multiplex assay for the detection of: $bla_{IMP-like}$, $bla_{OXA-like}$, $bla_{SHV-like}$, $bla_{TEM-like}$, and $bla_{ACC-like}$ genes with an IAC (FIG. 6A); and Non-template control sample showing the IAC melt peak for the multiplex reaction (FIG. 6B).

FIGS. 7A-7B—Shows high-resolution melting curves for the identification of $E.\ coli$ O157. FIG. 7A shows three different normalized melt profiles obtained using $E.\ coli$ O157 (ATCC Accession No. 43894), $E.\ coli$, and a mixture of two DNA samples (Mix). FIG. 7B shows a differential plot showing the differentiation of $E.\ coli$ O157 from other $E.\ coli$ and $Shigella$ strains.

BRIEF DESCRIPTION OF THE SEQUENCES

Figures 2A, 2B:
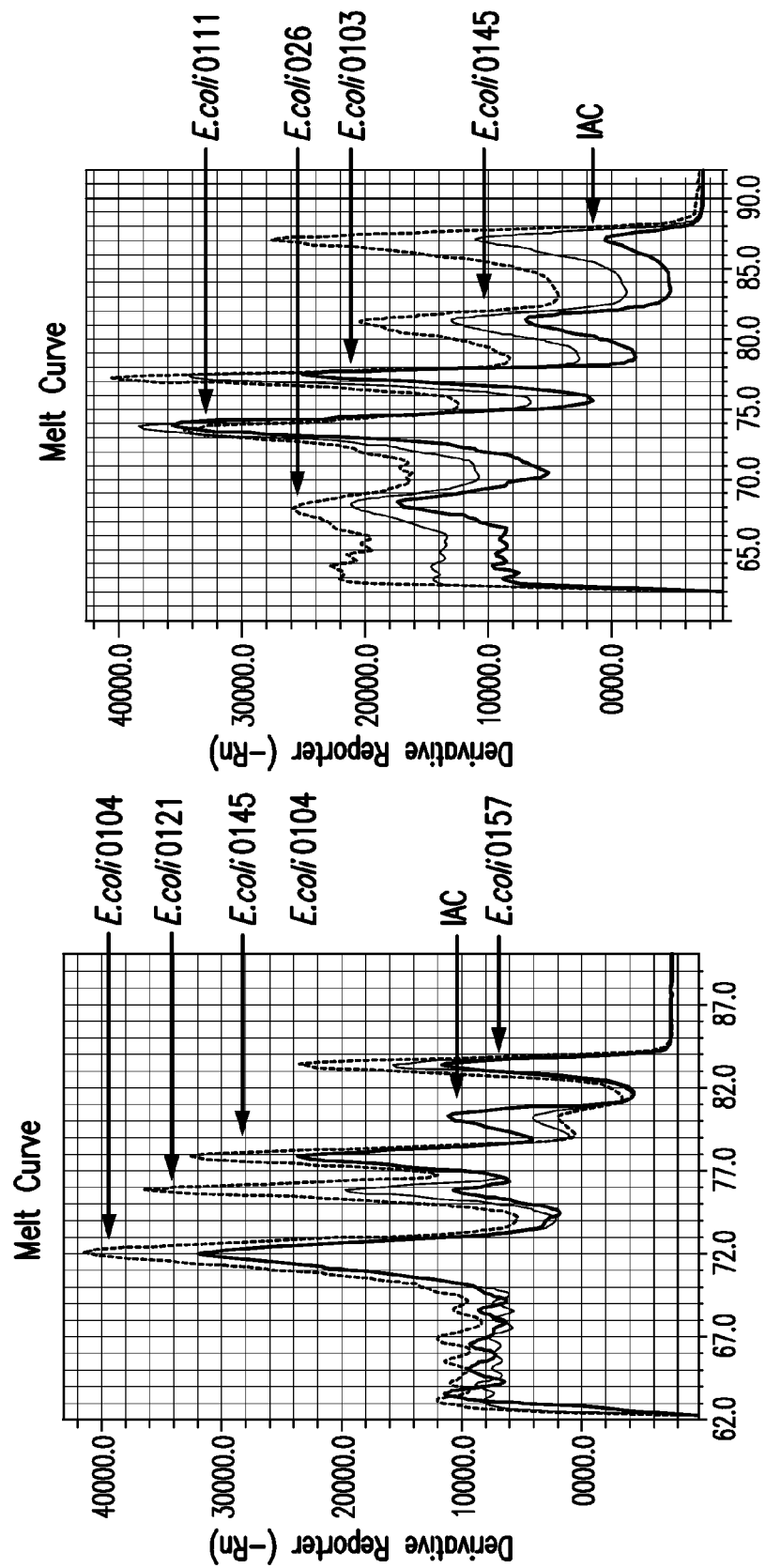
FIGS. 2A-2B—Shows a melt curve demonstrating the sensitivity of multiplex real-time PCR at different DNA concentration ranges.

SEQ ID NO:1-55—Primers used for real-time PCR assays to identify bacterial species in a biological sample.

DETAILED DESCRIPTION

The present invention provides methods for detecting and differentiating between multiple Shiga toxin-producing $Escherichia\ coli$ (STEC) in a biological sample based on specific melting temperatures ($T_m$) of polymerase chain reaction (PCR) amplicons specific to each STEC strain, the method comprising the steps of: i) enriching the bacterial concentration of the biological sample to result in an enriched sample; ii) isolating DNA from the enriched sample; and iii) detecting STEC sequences in the isolated DNA. In certain embodiments, methods of the present invention employ a two-step multiplex real-time PCR assay, which comprises an internal amplification control (IAC) to ensure robustness and to avoid false negative results, as well as DNA primers specific for each target bacterial strain or gene. In some embodiments, such methods may comprise multiplexed assays for detection of bacterial strains such as $E.\ coli$ O145, $E.\ coli$ O121, $E.\ coli$ O104, $E.\ coli$ O157, $E.\ coli$ O26, $E.\ coli$ O45, $E.\ coli$ O103, $E.\ coli$ O111, $Salmonella$, and other Gram-negative bacteria; virulence genes such as $stx_1$ and $stx_2$; or antibiotic resistance genes such as $bla_{KPC-like}$, $bla_{NDM-like}$, $bla_{CTX-M-1/2group}$, like, and $bla_{VIM-like}$, $bla_{IMP-like}$, $bla_{OXA-like}$, $bla_{SHV-like}$, $bla_{TEM-like}$, and $bla_{ACC-like}$ in said biological sample.

Methods currently available in the art for detection of bacterial strains in biological samples rely on conventional end-point PCR with subsequent visualization of amplified product using agarose gel electrophoresis, fluorescent probes, and/or antibody-based immunomagnetic separations to detect and distinguish between target strains, methods which are expensive, time consuming, and which have relatively short storage lives. The present invention does not rely on these methods and thus represents a significant improvement over the art. As described herein, the present invention uses specifically designed oligonucleotides to target specific DNA sequences and to generate PCR products with unique melting temperatures ($T_m$), making it a convenient and readily-accessible method for rapid and accurate screening of STECs or other bacterial species in biological samples. Additionally, the methods described herein require fewer reactions and shorter sample enrichment times than currently available methods. In some embodiments, such methods may also be performed in combination with other techniques known in the art, for example melt curve assays or other commercially available assays for virulence characterization or antibiotic resistance of isolated bacteria or serogroups.

STECs are zoonotic pathogens found in the intestinal tract and feces of beef cattle and ruminants, and thus can be introduced into food products of animal origin during slaughter. Beef products contaminated with animal feces have been associated with STEC infections in human. These pathogens have also been reported to contaminate milk, cheese, and other dairy products. STEC infections lead to a variety of illnesses with varying severity, including diarrhea, hemorrhagic colitis (bloody diarrhea), hemolytic uremic syndrome (kidney failure), and death resulting in STEC strains causing human illness to be included as notifiable pathogens to the Nationally Notifiable Diseases Surveillance System in 2000.

STECs are broadly divided into *E. coli* serotype O157 and non-O157 serogroups. In the last decade, the non-O157 serogroup has emerged as a major food-borne pathogen of concern worldwide, responsible for 63%, 74%, 82%, and 80% of the total STEC infections in Canada, Denmark, Germany, and the Netherlands, respectively. To date, a large number of STEC serogroups have been identified, but not all are pathogenic to humans. The frequency of infections of STEC serogroups is variable, with six non-O157 STEC serotypes being most commonly reported: O26 (26%), O103 (22%), O111 (19%), O121 (6%), O45 (5%), and O145 (4%), leading to their classification by the USDA as adulterants (zero tolerance) in non-intact raw beef products.

According to the Centers for Disease Control and Prevention (CDC), STECs led 14 foodborne outbreaks in the US from 2010 to 2014, with around 231,157 cases in the US annually. Of these, *E. coli* O157 led to 40.3% of infections, while non-O157 serogroups caused the remaining 59.7% cases. Another study of data collected from 2000 to 2010 by the USDA Food Safety and Inspection Service (FSIS) reported a total of 7,694 STEC-related cases, of which 5,688 (73.9%) were linked to the O157 serogroup, while as of 2006, 35.2% cases were caused by non-O157 STECs. Additionally, STEC serogroup O104 has been associated with sporadic cases of food-borne outbreaks in milk and sprouts. In 2011, *E. coli* O104:H4 led to a major multi-country outbreak in Europe, which was linked to the consumption of fenugreek sprouts. In the recent past, consumption of fresh produce and sprouts has increased and along with it, foodborne outbreaks associated with them. Detection of STECs in sprouts is a challenging task as the product has a high background microflora, the pathogen is internalized, and the presence of other coliforms can interfere with their detection.

STECs produce Shiga toxins via the expression of $stx_1$ and $stx_2$ genes, which are transferred to a bacterial cell by lambdoid phages that integrate into the bacterial chromosome. A total of 10 known stx subtypes are presently known. The $stx_1$ and $stx_2$ are further divided into multiple subtypes, in which $stx_1$ has three subtypes ($stx_{1a}$, $stx_{1c}$, and $stx_{1d}$), and $stx_2$ has seven subtypes ($stx_{2a}$, $stx_{2b}$, $stx_{2c}$, $stx_{2d}$, $stx_{2e}$, $stx_{2f}$, and $stx_{2g}$). Although commercial kits are presently available for identification of Shiga toxin genes, the high genetic diversity of the stx subtypes results in subtypes that may not necessarily be detected by the various assays (Feng et al., *Appl Environ Microbiol* 77:6699-6702, 2011; Margot et al., *J Food Protection* 76:871-873, 2013).

*Salmonella* is also one of the most important foodborne pathogens. According to the CDC FoodNet's most recent data (2013), *Salmonella* was responsible for the highest number of foodborne infections, accounting for 38% of all reported infections (15.19 per 100,000 population). So far in the years 2014-2015, fourteen *Salmonella* related outbreaks have been reported.

In addition to genes for the production of Shiga toxins in *E. coli* bacteria, genes coding for extended-spectrum β-lactamases (ESBLs) have been frequently isolated from the microbiota of food-producing animals (Mathew et al., *Foodborne pathogens and disease* 4:115-133, 2007; Sjölund-Karlsson et al., *Microbial drug resistance* 19:191-197, 2013), particularly in *E. coli* and *Salmonella* species. Among the different antibiotic groups, resistance to cephalosporins and carbapenems in the Enterobacteriaceae family has more severe consequences, particularly since recent surveillance data have shown their further increasing trend. The increase in frequency of ESBL- and carbapenemase-producing pathogens in livestock animals has gained considerable attention worldwide (Smet et al., *FEMS Microbiology Reviews* 34:295-316, 2010). The extensive use of these antibiotics in animal feedlots exerted a selective pressure leading to the evolution of and selection for ESBL genes. At present, ESBLs are divided into more than ten enzyme families, including CTX-M, SHV, TEM, PER, VEB, BES, GES, TLA, SFO, and OXA. ESBL-encoding genes act as one of the most influential mechanisms for cephalosporin resistance in members of the Enterobacteriaceae, particularly *Salmonella, E. coli,* and *Klebsiella pneumoniae*. Recent data from the National Antimicrobial Resistance Monitoring System (NARMS) have shown an increase in third generation cephalosporin resistance among *Salmonella* Heidelberg isolated from livestock animals at slaughter (chicken, turkey), retail meat (chicken breast, pork chop, ground turkey), and humans (Folster et al., *Foodborne pathogens and disease* 9:638-645, 2012).

The CTX-M enzymes are one of the biggest and most diverse groups among the ESBL family with more than 150 CTX-M variants, and exhibit strong hydrolytic activity against aztreoman, cefotaxime, and ceftriaxone, and partially against ceftazidime. The diversity of CTX-M enzymes varies with geographical locations, but CTX-M-15 and CTX-M-14 (followed by CTX-M-2, CTX-M-3, and CTX-M-1) are the most common enzymatic variants worldwide among all major clinically important pathogens (Zhao et al., *Critical reviews in microbiology* 39:79-101, 2013). Apart from the ESBLs that belong to the class A β-lactamases, the class C β-lactamases (AmpC) confer resistance towards third-generation cephalosporins and ESBL inhibitors (Bush et al., *Antimicrobial Agents and chemotherapy* 54:969-976, 2010). The AmpC genes are located on the chromosome in various Enterobacteriaceae members, including *Citrobacter* spp., *Enterobacter* spp., *E. coli, Morganella morgannii* and *Hafnia alvei*. However, plasmid-encoded AmpC (pAmpC), such as CMY, ACC, and DHA occur in *E. coli, K. pneumoniae,* and *Proteus mirabilis*. CMY-2 is the most prevalent pAmpC in the Enterobacteriaceae family (Smet et al., *FEMS Microbiology Reviews* 34:295-316, 2010).

Carbapenemase enzymes are produced by pathogenic bacteria to degrade and neutralize the effects of almost all β-lactam antibiotics, including carbapenems (Cantón et al., *Clinical Microbiology and Infection* 18:413-431, 2012). The class A carbapenemases, such as IMI, NMC, SME, KPC, and GES, confer resistance to the carbapenems at various levels, ranging from complete resistance to reduced susceptibility (Queenan et al., *Clinical microbiology reviews* 20:440-458, 2007). OXA-48, OXA-23, OXA-24, and OXA-58 are the most dominant class D carbapenemases in *K. pneumoniae* and *A. baumannii*. The metallo-β-lactamases (class B carbapenemases), including the GIM, IMP, NDM, SIM, and VIM enzymes, are mainly encoded on conjugative plasmids in the Enterobacteriaceae, *Pseudomonas aeruginosa,* and *A. baumannii* (Nordmann et al., *Emerging Infectious Diseases* 17:1791-1798, 2011). Of these five enzymes, IMP, NDM, and VIM are the most prevalent enzyme groups among the metallo-β-lactamases.

In accordance with the invention, eight different serotypes of STEC, including all of the non-O157 serogroups classified as adulterants in the United States, and an additional serotype, O104, implicated in a major 2011 European outbreak linked to sprouts, can be specifically and reliably detected in a biological sample. This number of targets as described herein is much greater than any other assays currently available. In one embodiment, STEC serotypes that may be detected by the methods of the invention include, but are not limited to, O145, O121, O104, O157, O26, O45, O103, and O111. In another embodiment, the methods of the present invention may identify and distinguish between additional pathogens, including, but not limited to, virulent strains of *Salmonella*, which lead to the second highest number of foodborne infections in the United States, or antibiotic-resistant strains of bacteria. Using the methods described herein, these STEC and/or other types of pathogenic bacteria may be specifically and reliably detected in a biological sample at low concentrations and in minimal time, thus enabling rapid and low-cost simultaneous detection of multiple pathogenic bacteria.

The methods described herein may be used to test a multitude of biological samples, for example food products. In one embodiment, a biological sample may be meat such as beef, beef stew meat, beef trimmings, chicken, turkey, or the like. A biological sample may also include produce such as various vegetables and fruits, such as alfalfa sprouts, spinach, lettuce, or juices from vegetable or fruits such as apple cider. As used herein, a "biological sample" or "sample" may also include clinical samples such as blood and blood parts including, but not limited to serum, plasma, platelets, or red blood cells; sputum, mucosa, tissue, cultured cells, including primary cultures, explants, and transformed cells; biological fluids, stool, and urine. A biological sample may also include sections of tissues such as biopsy and autopsy samples, and frozen sections taken for histologic purposes. A biological sample may be obtained from a eukaryotic organism, for example a mammal, including humans, cows, pigs, chickens, turkeys, ducks, geese, dogs, goats, and the like. Any tissue appropriate for use in accordance with the invention may be used, for instance, skin, brain, spinal cord, adrenals, pectoral muscle, lung, heart, liver, crop, duodenum, small intestine, large intestine, kidney, spleen, pancreas, adrenal gland, bone marrow, lumbosacral spinal cord, or blood.

In some embodiments, methods of the present invention may comprise the steps of: i) enriching a bacterial concentration in a test sample by incubating the sample aerobically at approximately 42° C., for instance 37° C., 38° C., 39° C., 40° C., 41° C., 42° C., 43° C., 44° C., or 45° C. in an enrichment media such as described herein; ii) isolating DNA from the enriched sample; and iii) detecting sample DNA via real-time PCR employing a two-step multiplex assay with internal amplification controls (IAC) and specific primer sets as described herein.

During the sample enrichment step, a biological sample such as a food sample or other clinical sample, may be collected and diluted in a buffer or media such as water, saline, brain heart infusion broth (BHI), tryptic soy broth (TSB), or sterile Buffered Peptone Water (BPW), among others. Media useful for culture or enrichment of STECs, *Salmonella*, or other food pathogens in food samples would be known by one of skill in the art. Exemplary media in accordance with the invention may include, but are not limited to, BHI, TSB, and buffered peptone water (BPW) broth. In some embodiments, a sample as described herein may be diluted at any stage in a desired buffer or solution, for example 1:10, 1:9, 1:8, 1:7, 1:6, 1:5, 1:4, 1:3, 1:2, or 1:1.

Antibiotics may be used in the enrichment of STECs, *Salmonella*, or other food pathogens in order to provide a selective advantage for pathogens to grow among any other bacteria present in a food or environmental sample. The use of antibiotics in enrichment broth may hinder the growth of other existing bacteria and simultaneously promote the selective growth of pathogens to be detected in the assay of the present invention. Selection of suitable antibiotics may ensure that the growth of the selected pathogen is not inhibited, thereby ensuring that the sample enrichment time is not lengthened unnecessarily. In some embodiments, antibiotics may be added to a sample or medium such as an enrichment medium or a culture medium. For example VCC supplement, containing vancomycin, which deters the growth of Gram-positive bacteria, cefixime, which suppresses the growth of *Proteus* spp., and/or cefsulodin, which inhibits *Pseudomonas* spp.; novobiocin, acriflavine, penicillin, streptomycin, chloramphenicol, gentamycin, and the like. Antimycotic compounds may include, but are not limited to Fungizone or other suitable compound. Any of these compounds may be used alone or in combination where appropriate. Any suitable concentration of antibiotic or antimycotic may be used, for example 10 mg/L, 9 mg/L, 8 mg/L, 7 mg/L, etc. In other embodiments, a diluted sample may be homogenized using an appropriate device, such as a Stomacher, for a short time period (such as 2 minutes) in order to release attached cells. The homogenized samples may be incubated aerobically, such as at 42° C. or other temperature suitable for a bacterial strain, for anywhere from 4 to 12 hours to allow for enrichment (recovery and growth of target bacterial species). For example, samples may be incubated for 4 hours, 5 hours, 6 hours, 7 hours, 8 hours, 9 hours, 10 hours, 11 hours, or 12 hours, or the like.

During the DNA isolation step as described herein, DNA from an enriched sample may be isolated using any method available as would be known by one of skill in the art. In one embodiment, a commercially available kit, such as PrepMan® Ultra Sample Preparation Reagent (Applied Biosystems, Life Technologies) may be used to isolate DNA. According to one embodiment, suspended food particles may be separated from the media, for instance through filtration or centrifugation of the enriched sample, for example at 100×g. The obtained supernatant may then be used for DNA isolation as described herein.

Isolation and Amplification of DNA

Methods such as polymerase chain reaction (PCR and RT-PCR) and ligase chain reaction (LCR) may be used to amplify nucleic acid sequences directly from genomic material, such as genomic DNA, mRNA, cDNA, or from genomic libraries, or cDNA libraries.

In some embodiments, an amplicon of the invention may be detected using a PCR-based detection method, where the size, sequence, or melting temperature of the PCR amplicon is indicative of the absence or presence of the pathogen, bacteria, or gene to be detected. Real-time PCR technology amplifies and simultaneously detects and/or quantifies a target DNA molecule. In these types of methods, PCR primers are hybridized to the regions flanking a target sequence. It will be appreciated that, although many specific examples of primers are provided herein, suitable primers to be used with the invention can be designed using any suitable method. It is not intended that the invention be limited to any particular primer or primer pair.

In some embodiments, the primers are not labeled, and the amplicons may be visualized, detected, and/or analyzed following their melting temperature, for example by generation of melt curve assays or plots. In other embodiments, an amplicon may be visualized according to size, e.g., using agarose gel electrophoresis. In some embodiments, ethidium bromide staining of the PCR amplicons following size resolution allows visualization of the different size amplicons. Such an approach may be referred to as end-point PCR. Conventional end-point PCR, while suitable for amplification and detection of a target DNA or sequence, may require extensive sample enrichment time due to the higher copy number of target DNA molecules needed for detection. This translates to a higher number of target cells, which, in turn, translates to longer enrichment times. In some embodiments, the primers of the invention may be radiolabelled, or labeled by any suitable means (e.g., using a non-radioactive fluorescent tag), to allow for rapid visualization of amplicons of different sizes following an amplification reaction without any additional labeling step or visualization step.

It is not intended that the primers of the invention be limited to generating an amplicon of any particular size. For example, the primers used to amplify a bacterial gene or sequence described herein are not limited to amplifying the entire region of a relevant locus. A primer can generate an amplicon of any suitable length that is longer or shorter than those disclosed herein. In some embodiments, amplification of a target sequence may produce an amplicon at least 20 nucleotides in length, or alternatively, at least 50 nucleotides in length, or alternatively, at least 100 nucleotides in length, or alternatively, at least 200 nucleotides in length. Target sequences in addition to those recited herein may also find use with the present invention.

In accordance with the invention, a PCR assay as described herein may be multiplexed in order to combine multiple reactions into a single assay. For example, a multiplex assay may enable amplification of multiple target sequences using a number of PCR primer pairs, such as one or more primers set forth in the Examples. One of skill in the art will understand that the reaction conditions for each individual reaction in a multiplex assay will necessarily be similar in order to achieve efficient amplification of each target. Optimization or other testing of each individual primer pair may be necessary. For the development of a multiplex PCR assay such as described herein, a large number of primer-pairs has to be tested for each target in order to determine the optimum primer that will produce the best result. Out of multiple PCR primers that work for a particular multiplex assay, a final set of primer pairs for a multiplex assay may be selected based on specific criteria, including, but not limited to, (1) maximum melting temperature difference (at least 2-3° C.) from neighboring peaks; (2) higher PCR amplification efficiency; (3) amplicon size; and (4) size of melt peak formed on the melt curve plot. In accordance with the invention, specific primers may be designed such that the melting temperature ($T_m$) of a PCR amplicon is maintained between approximately 67° C. to 87° C. For example, the melting temperature of amplicons may be approximately 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., or 87° C. Additionally, in some embodiments, each amplicon $T_m$ may be separated from other amplicons in the multiplex assay by approximately 2-3° C. In other embodiments, serotype-specific primer pairs may be designed based on any appropriate bacterial gene. For example, O-antigen gene clusters of E. coli encode the wzx O-antigen flippase and wzy O-antigen polymerase, which are involved in the synthesis of unique amino acid sequences of O-antigens located on the surface of E. coli outer membrane (Lin et al., Food Microbiol 28(3):478-483, 2011). As a result, these genes may serve as excellent targets for detection of non-O157 STECs at the serotype level. Additional genes for detection of O157 bacterial species and/or other pathogenic bacteria or antibiotic resistant bacteria may be designed for use with the methods of the present invention, as described herein. Multiplex assays targeting serotype-specific O-antigen cluster genes for the detection of multiple strains of STECs have been previously described (Bai et al., Foodborne Pathog Dis 9(6): 541-548, 2012; Fratamico et al., Foodborne Pathog Dis 8(5):601-607, 2011; Valadez et al., J Food Protect 74(2):228-239, 2011). Thus, in certain embodiments, the wzx gene encoding a flippase may be used for designing STEC-specific primers, or the glycosyl transferase gene may be used for designing specific primer pairs for E. coli O104. The uidA gene primer designed by Cebula et al. (J Clin Microbiol 33(1):248-250, 1995) and Wang et al. (Appl Environ Microb 78(8):2727-2736, 2007) was used for detection of E. coli O157:H7. One of skill in the art will understand that any other suitable bacterial genes such as those described herein and in the Examples may be used in accordance with the invention. Any suitable software may be used for primer design, such as Primer3 software (Untergasser et al., 2012). In addition, the specificity of designed PCR primers may be tested, for example, using the NCBI/Primer-BLAST tool, and the $T_m$ of amplicons may be estimated using BioEdit software (Hall, Nucl Acids 41:95-98, 1999).

In some embodiments, a bacterial species such as a STEC or other pathogenic or antibiotic resistant bacterial species as described herein may be detected based on the level of a particular RNA or DNA in a biological sample. Any of the primers described herein and set forth as SEQ ID NOs:1-55 may be used for detection, diagnosis, and determination of the presence of such a bacterial species. Any suitable primer may be used to detect genomic DNA or any sequence therein, an open reading frame or gene, or a protein of choice, using any appropriate methods known in the art. A suitable nucleic acid sequence may be used as single- or double-stranded probes or primers for detection of nucleic acid of a STEC or other desired bacterial species, or cDNA generated therefrom, as may be present in a biological sample. Polynucleotides from a bacterial species as described herein may also be used to generate additional copies of the polynucleotides, in order to generate antisense oligonucleotides, or as triple-strand forming oligonucleotides. For example, two oligonucleotide primers may be used in a PCR-based assay to amplify a portion of a bacterial gene sequence or cDNA derived from a biological sample, wherein at least one of the oligonucleotide primers is specific for (i.e., hybridizes to) the bacterial polynucleotide. Such primers may be any length sufficient to hybridize to and enable amplification of a bacterial nucleic acid as described herein, including at least or about 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 35 nucleotides, 40 nucleotides, 45 nucleotides, or 50 nucleotides; or from about 12 to about 50 nucleotides in length, 15 to 30 nucleotides in length, 15 to 25 nucleotides in length, or 20 to 30 nucleotides in length. DNA primers suitable for use with the present invention may be any primers described herein, such as those set forth as SEQ ID NOs:1-55. An amplified nucleotide may then be detected and distinguished for other sequences using techniques described herein.

A PCR assay may include a number of reagents and components, including a master mix and nucleic acid dye or intercalating agent. In some embodiments, an exemplary PCR master mix may contain template genomic material, such as DNA, PCR primers, salts such as $MgCl_2$, a polymerase enzyme, and deoxyribonucleotides. One of skill in the art will be able to identify useful components of a master mix in accordance with the present invention. In one embodiment, a master mix such as MeltDoctor™ HRM Master Mix (Applied Biosystems, Life Technologies), which contains the high resolution melting (HRM) dye, SYTO®9 may be used.

During real-time PCR detection, PCR may be performed in any reaction volume, such as 10 μL, 20 μL, 30 μL, 50 μL, 100 μL, or the like. Reactions may be performed singly, in duplicate, or in triplicate. PCR thermal cycling conditions are well known in the art and vary based on a number of factors. As described herein, an exemplary two-step amplification protocol may include, for example, an initial denaturation at 94° C. for 10 min; 40 cycles of 94° C. for 30 s, 60° C. for 45 s; and a melt curve step performed at the end of the PCR (from 60° C. to 95° C., with gradual temperature increments of 0.04-0.1° C./s). Melt curve plots may be prepared by plotting the negative derivative of fluorescence (-Rn) versus temperature. Mean $T_m$ values for each product may be calculated by averaging the $T_m$ values from duplicate runs of two replications. Any thermal cycling program may be designed as appropriate for use with the particular primers for detection of particular bacterial species as would be understood by one of skill in the art.

Test samples or assays as described herein may be compared to a control or reference sample, such as a positive control, in order to accurately determine the presence and/or amount of a particular pathogen such as a STEC or pathogenic or antibiotic resistant bacterial species. In addition, a reaction control may be used, such as an internal amplification control (IAC), in order to avoid false negative results and thereby increase the reliability of an assay. Use of an IAC in a reaction provides assurance that a negative result for a target is truly a negative result rather than due to a problem or break-down in the reaction. Because the signal for the IAC should always be generated, even when the target signal is not generated (i.e., the target organism or DNA is not present in the sample), this would indicate that a negative target signal is indeed a negative result. An IAC may be useful in diagnostic assays because food matrices may harbor inhibitory components that may interfere with PCR amplification, leading to false negative results.

During a real-time PCR detection step, an IAC and primer sets may be designed such that they are specific for a particular pathogen to be detected. For example, an IAC can be designed from 16S rDNA, plasmid DNA, phage DNA, the 16S rRNA gene of gamma proteobacteria, or the like. Alternatively, according to one embodiment of the invention, single stranded synthetic oligonucleotides may be employed as an IAC in a real-time PCR assay. In certain embodiments, specific primers may be designed to amplify an IAC to be used in an assay. In one embodiment, IAC oligonucleotides may be designed such that they may be co-amplified by a primer pair already present in the particular multiplex reaction mixture. For example, as described in the Examples, IAC-104121145157 (SEQ ID NO:9) may be amplified by primers O121-F-716 (SEQ ID NO:3) and O121-R-865 (SEQ ID NO:4), or IAC-2611110345 (SEQ ID NO:18) may be amplified using primers O111-F-287 (SEQ ID NO:16) and O111-R-371 (SEQ ID NO:17). In another embodiment, IAC-O157-set-121pp (SEQ ID NO:23) may be amplified by primers O121-F-716 (SEQ ID NO:3) and O121-R-865 (SEQ ID NO:4), or IAC-Sal-set-103pp (SEQ ID NO:31) may be amplified by primers O103-F-752 (SEQ ID NO:14) and O103-R-920 (SEQ ID NO:15). In still another embodiment, IAC-NDM-pp (SEQ ID NO:42) may be amplified by primers NDM-310-F (SEQ ID NO:34) and NDM-559-R (SEQ ID NO:35), or IAC-SHV-pp (SEQ ID NO:53) may be amplified by primers SHV-309-F (SEQ ID NO:47) and SHV-503-R (SEQ ID NO:48). Such an approach may facilitate in minimizing the total number of primer pairs used for a multiplex assay.

Short oligonucleotides such as an IAC molecule as described herein may be amplified at a much higher amplification efficiency (>100%) and thus may be preferentially amplified in a multiplex PCR reaction. To overcome this issue, an IAC molecule may be added to a multiplex reaction at the lowest possible concentration (10-20 fg), facilitating preferential amplification of the desired target DNA.

In accordance with the invention, IAC oligonucleotides as described herein may be added to a PCR reaction or assay at any concentration suitable for the assay. In some embodiments, the concentration of an IAC may be very low, such as 10 fg or 100 fg per 10 μL reaction, for example 1 fg, 2 fg, 3 fg, 4 fg, 5 fg, 10 fg, 20 fg, 30 fg, 50 fg, 75 fg, 85 fg, 90 fg, or 100 fg per 10 μL reaction. Lower concentrations of IAC oligonucleotides may allow preferential amplification of pathogenic genomic DNA or target sequences to be detected, and in the process, the size of the IAC peak generated in a multiplex reaction may be smaller when compared with other peaks. In the case of a negative control, the size of the IAC peak may be bigger because all of the primers are available for its amplification.

Modification of Nucleic Acids

Any number of methods well known to those skilled in the art can be used to isolate and manipulate a DNA molecule. For example, as previously described, PCR technology may be used to amplify a particular starting DNA molecule and/or to produce variants of the starting DNA molecule. DNA molecules, or fragments thereof, can also be obtained by any techniques known in the art, including directly synthesizing a fragment by chemical means. Thus, all or a portion of a nucleic acid as described herein may be synthesized.

As used herein, the term "complementary nucleic acids" refers to two nucleic acid molecules that are capable of specifically hybridizing to one another, wherein the two molecules are capable of forming an anti-parallel, double-stranded nucleic acid structure. In this regard, a nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional "low-stringency" conditions. Similarly, the molecules are said to be complementary if they can hybridize to one another with sufficient stability to permit them to remain annealed to one another under conventional "high-stringency" conditions. Conventional stringency conditions are known in the art and described by Sambrook, et al. (1989), and by Haymes et al. (1985).

Departures from complete complementarity are permissible, as long as the capacity of the molecules to form a double-stranded structure remains. Thus, in order for a nucleic acid molecule or a fragment of the nucleic acid molecule to serve as a primer or probe, such a molecule or fragment need only be sufficiently complementary in sequence to be able to form a stable double-stranded structure under the particular solvent and salt concentrations employed.

Appropriate stringency conditions that promote DNA hybridization are well known to one of skill in the art and may include, for example, 6× sodium chloride/sodium citrate (SSC) at about 45° C., followed by a wash of 2×SSC at 50° C. The salt concentration in the wash step may be selected from a low stringency of approximately 2×SSC at 50° C. to a high stringency of about 0.2×SSC at 50° C. The temperature in the wash step may be increased from low stringency conditions at room temperature, about 22° C., to high stringency conditions at about 65° C. The temperature and/or salt conditions may be varied as appropriate for optimum results. In accordance with the invention, a nucleic acid may exhibit at least from about 80% to about 100% sequence identity with one or more nucleic acid molecules as described herein, for example at least from about 80%, about 85%, about 90%, about 95%, about 98%, about 99%, or about 100% sequence identity. One of skill in the art will understand that stringency may be altered as appropriate to ensure optimum results.

As used herein, the terms "sequence identity," "sequence similarity," or "homology" are used to describe sequence relationships between two or more nucleotide sequences. The percentage of "sequence identity" between two sequences is determined by comparing two optimally aligned sequences over a specific number of nucleotides, wherein the portion of the sequence in the comparison window may comprise additions or deletions (i.e., gaps) as compared to a reference sequence. Two sequences are said to be identical if nucleotides at every position are the same. A nucleotide sequence when observed in the 5' to 3' direction is said to be a "complement" of, or complementary to, a second nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

Detecting the Presence of a Bacterial Species in a Biological Sample

In some embodiments, a polynucleotide of the invention may be detectably labeled. Detectable labels may include, but are not limited to, radiolabels, fluorochromes, including fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxy fluorescein (5-FAM) or N,N,N',N'-tetramethyl-6-carboxyrho-damine (TAMRA); radioactive labels such as $^{32}P$, $^{35}S$, and $^{3}H$), and the like. In some embodiments, a detectable label may involve multiple steps (e.g., biotin-avidin, hapten-anti-hapten antibody, and the like). A primer useful in accordance with the invention may be identical to a particular bacterial target nucleic acid sequence and different from other bacterial sequences. In another embodiment, a primer and/or probe useful in accordance with the invention may enable distinction between a nucleic acid sequence from a STEC in the O157 serogroup and a nucleic acid sequence from a STEC in the non-O157 serogroup. In another embodiment, primers and/or probes may enable distinction between pathogenic and non-pathogenic bacterial species, or to identify antibiotic resistant bacterial species in a biological sample.

In accordance with the invention, any suitable qualitative or quantitative methods known in the art for detecting specific bacterial nucleic acids (e.g., RNA or DNA) may be used. A bacterial nucleic acid may be detected by, for example, in situ hybridization in tissue sections, using methods that detect single base pair differences between hybridizing nucleic acid, by reverse transcriptase-PCR, or in northern blots containing poly A mRNA, or other methods well known in the art. For detection of bacterial polynucleotides in blood or blood-derived samples, methods that allow for detection of single base pair mismatches may be employed.

Diagnostic Tests and Kits

The invention further provides diagnostic reagents and kits comprising one or more such reagents or components for use in a variety of diagnostic assays, including for example, nucleic acid assays, e.g., PCR or RT-PCR assays. Such kits may preferably include at least a first primer pair as described herein, and means for detecting or visualizing amplification of a target sequence. In some embodiments, such a kit may contain multiple primer pairs as described herein for the purpose of performing multiplex PCR or RT-PCR for detection of multiple target sequences. Primer pairs may be provided in lyophilized, dessicated, or dried form, or may be provided in an aqueous solution or other liquid media appropriate for use in accordance with the invention.

Kits may also include additional reagents, e.g., PCR components, such as salts including $MgCl_2$, a polymerase enzyme, and deoxyribonucleotides, and the like, reagents for DNA isolation, or enrichment of a biological sample, including for example media such as water, saline, BHI, TSB, BPW, or the like, as described herein. Such reagents or components are well known in the art. Where appropriate, reagents included with such a kit may be provided either in the same container or media as the primer pair or multiple primer pairs, or may alternatively be placed in a second or additional distinct container into which the additional composition or reagents may be placed and suitably aliquoted. Alternatively, reagents may be provided in a single container means.

Definitions

As used herein, "STEC" or "Shiga toxin-producing *Escherichia coli*" refers to a group of *E. coli* strains with the ability to produce Shiga toxin via the expression of stx1 and stx2 genes. STECs are broadly divided into *E. coli* serotype O157 and non-O157 serogroups.

As used herein, "multiplex" refers to refers to the use of PCR to amplify several different DNA targets (genes) simultaneously in a single assay or reaction. Multiplexing can amplify nucleic acid samples, such as genomic DNA, cDNA, RNA, etc., using multiple primers and any necessary reagents or components in a thermal cycler.

As used herein, "enrichment" refers to conditions favoring the growth of a particular microorganism. For example, in one embodiment, a method of the present invention may benefit from an enrichment step whereby bacterial cells or a solution obtained by homogenizing a biological sample and containing one or more target bacterial cells or species are placed in an enrichment medium to allow for the growth of the target bacterial species or strains for the purposes of detection of the bacterial cells or species.

As used herein, the term "subject," "patient," or "organism" includes humans and mammals (e.g., mice, rats, pigs, cats, dogs, and horses). Typical subjects for which methods of the present invention may be applied will be mammals, such as humans. A wide variety of subjects will be suitable for veterinary, diagnostic, research, or food safety applications, e.g., humans; livestock such as cattle, sheep, goats, cows, swine, and the like; poultry such as chickens, ducks, geese, turkeys, and the like; and domesticated animals, particularly pets such as dogs and cats. The term "living subject" refers to a subject as noted above or another organism that is alive.

As used herein, the term "culture media" or "media" refers to liquid, semi-solid, or solid media used to support bacterial cell growth in a non-native environment. Further, by culture media is meant a sterile solution that is capable of sustaining and/or promoting the division or survival of such cells. Suitable culture media are known to one of skill in the art, as discussed herein. The media components may be obtained from suppliers other than those identified herein and may be optimized for use by those of skill in the art according to their requirements. Culture media components are well known to one of skill in the art and concentrations and/or components may be altered as desired or needed.

In certain embodiments, sequences of the present invention, including primer sequences, target sequences and IAC sequences may be identical to the sequences provided here in or comprise less than 100% sequence identity to the sequences provided herein. For instance, primer sequences, target sequences or IAC sequences of the present invention may comprise 90% identity to the sequences provided herein. The terms "identical" or "percent identity," in the context of two or more nucleic acids or sequences, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., the NCBI web site found at ncbi.nlm.nih.gov/BLAST/ or the like). Such sequences are then referred to as "substantially identical." This definition also refers to, or applies to, the compliment of a particular sequence. The definition may also include sequences that have deletions, additions, and/or substitutions. To compensate for gene sequence diversity and to target multiple gene variants of the same genes, degenerated primer pairs (1-2 bases or approximately 5-10% alterations) are allowed.

For sequence comparison, one sequence typically serves as a reference sequence, to which other sequences are compared. When using a sequence comparison algorithm, reference and comparison sequences may be entered into a computer, and sequence algorithm program parameters are selected as desired. Percent sequence identities are then generated for the comparison sequences relative to the reference sequence, based on the parameters selected. An example of an algorithm that may be suitable for determining percent sequence identity and sequence similarity are the BLAST and BLAST 2.0 algorithms, which are described in Altschul et al., (*Nuc Acids Res* 25:3389-3402, 1977) and Altschul et al., (*J Mol Biol* 215:403-410, 1990), respectively. BLAST and BLAST 2.0 are well known in the art and may be used to determine percent sequence identity for any nucleic acids, such as those described herein.

As used herein, the term "nucleic acid" refers to a single or double-stranded polymer of deoxyribonucleotide bases or ribonucleotide bases read from the 5' to the 3' end, which may include genomic DNA, target sequences, primer sequences, or the like. In accordance with the invention, a "nucleic acid" may refer to any DNA or nucleic acid to be used in an assay as described herein, which may be isolated or extracted from a biological sample. The term "nucleotide sequence" or "nucleic acid sequence" refers to both the sense and antisense strands of a nucleic acid as either individual single strands or in the duplex. The terms "nucleic acid segment," "nucleotide sequence segment," or more generally, "segment," will be understood by those in the art as a functional term that includes genomic sequences, target sequences, operon sequences, and smaller engineered nucleotide sequences that express or may be adapted to express, proteins, polypeptides or peptides. The nomenclature used herein is that required by Title 37 of the United States Code of Federal Regulations § 1.822 and set forth in the tables in WIPO Standard ST.25 (1998), Appendix 2, Tables 1 and 3.

The term "gene" refers to components that comprise bacterial DNA or RNA, cDNA, artificial bacterial DNA polynucleotide, or other DNA that encodes a bacterial peptide, bacterial polypeptide, bacterial protein, or bacterial RNA transcript molecule, introns and/or exons where appropriate, and the genetic elements that may flank the coding sequence that are involved in the regulation of expression, such as, promoter regions, 5' leader regions, 3' untranslated region that may exist as native genes or transgenes in a bacterial genome. The gene or a fragment thereof can be subjected to polynucleotide sequencing methods that determines the order of the nucleotides that comprise the gene. Polynucleotides as described herein may be complementary to all or a portion of a bacterial gene sequence, including a promoter, coding sequence, 5' untranslated region, and 3' untranslated region. Nucleotides may be referred to by their commonly accepted single-letter codes.

The term "recombinant" when used with reference, e.g., to a cell, or nucleic acid indicates that the cell or nucleic acid has been modified by the introduction, by natural or artificial means, of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. In some embodiments, recombinant sequences may also include nucleic acids, proteins, or recombinant genomes, such as bacterial genomes. In certain embodiments, a "recombinant" bacterium or cell may refer to a bacterial cell into which a stx gene or nucleic acid has been inserted, for example by a lambdoid phage, conferring the ability of the bacterial cell to produce shiga toxin.

The term "about" is used herein to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When not used in conjunction closed wording in the claims or specifically noted otherwise, the words "a" and "an" denote "one or more." The term "conferred by a transgene," for example, thus encompasses one or more transgene(s).

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

While the invention has been described in connection with specific embodiments thereof, it will be understood that the present invention is capable of further modifications by one of skill in the art. It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. The present disclosure is therefore intended to encompass any variations, uses, or adaptations of the invention following, in general, the principles of the invention and including such departures from the present disclosure as come within known or customary practice within the art to which the invention pertains and as may be applied to the essential features herein before set forth.

EXAMPLES

Example 1

Multiplex Real-Time PCR Assay for the Detection of Eight Shiga Toxin-Producing *Escherichia coli* Using Melting Curve Analysis Bacterial Strains:

A standard non-O157 STEC reference culture set was procured from the STEC Center at Michigan State University (Michigan, USA) (Table 1). *E. coli* O157:H7 strains were obtained from the University of Missouri Food Microbiology Lab culture collection. Cultures were grown at 37° C. in Tryptic Soy broth (TSB) (Difco Labs., MD, USA). The cultures were maintained at a temperature of −50° C. in TSB (Difco Labs., MD, USA) supplemented with 30% glycerol.

TABLE 1

E. coli strains used in this study

| | Serotype | Strain |
|---|---|---|
| 1. | E. coli O 26:H11 | DEC10B |
| 2. | E. coli O 26:H11 | 97-3250 |
| 3. | E. coli O 26:H | MT#10 |
| 4. | E. coli O 26:H N | TB352A |
| 5. | E. coli O 45:H2 | M103-19 |
| 6. | E. coli O 45:H2 | MI01-88 |
| 7. | E. coli O 45:H2 | MI05-14 |
| 8. | E. coli O 45:H NM | DA-21 |
| 9. | E. coli O 103:H2 | MT#80 |
| 10. | E. coli O 103:H6 | TB154A |
| 11. | E. coli O 103:H25 | 8419 |
| 12. | E. coli O 103:H N | PT91-24 |
| 13. | E. coli O 111:H2 | RD8 |
| 14. | E. coli O 111:H8 | 3215-99 |
| 15. | E. coli O 111:H11 | 0201 9611 |
| 16. | E. coli O 111:H NM | 3007-85 |
| 17. | E. coli O 121:H19 | 3377-85 |
| 18. | E. coli O 121:H19 | MT#2 |
| 19. | E. coli O 121:H | MT#18 |
| 20. | E. coli O 121:H[19] | DA-5 |
| 21. | E. coli O 145:H NT | D177 |
| 22. | E. coli O 145:H[28] | 4865/96 |
| 23. | E. coli O 145:H NM | GS G5578620 |

TABLE 1-continued

E. coli strains used in this study

| | Serotype | Strain |
|---|---|---|
| 24. | E. coli O 145:H NT | IH 16 |
| 25. | E. coli O 104:H | ECOR 228 |
| 26. | E. coli O 104:H | TW04909 |
| 27. | E. coli O 104:H | TW04911 |
| 28. | E. coli O 104:H | TW01435 |
| 29. | E. coli O 157:H7 | 505B |
| 30. | E. coli O 157:H7 | 3178-85 |
| 31. | E. coli O 157:H7 | 43894 |
| 32. | E. coli O 157:H7 | C7927 |
| 33. | E. coli O 157:H7 | MF 1847 |

Bacterial DNA Extraction:

Genomic DNA from all bacterial isolates used in the study and from enriched food samples was isolated using PrepMan® Ultra Sample Preparation Reagent (Applied Biosystems, Foster City, Calif., USA) according to the manufacturer's instructions. The concentrations and purity of the obtained DNA samples was determined using a Nanodrop 2000 spectrophotometer (Thermo Fisher Scientific, Wilmington, Del., USA).

Primer Design:

PCR primers used in this study were designed using the Primer3 software (Untergasser et al., *Nucleic Acids Research* 40:e115-e115, 2012). Serotype-specific primer pairs for the identification of six STEC serotypes were designed based on the wzx gene, which encodes a flippase, and serotype-specific primer pairs for amplification of *E. coli* O104 were designed based on the glycosyl transferase gene sequence (Tables 2 and 3). The uidA gene primer designed by Cebula et al. (*J Clin Microbiol* 33:248-250, 1995) was used for detection of *E. coli* O157:H7. The oligonucleotides were commercially synthesized (IDT, Coraville, Iowa, USA). Primers were designed to keep the melting temperature ($T_m$) of the PCR amplicons between 67° C. to 87° C. and each amplicon $T_m$ separated from other amplicon in multiplex assay by approximately 2-3° C. The specificity of the designed PCR primers was tested using the NCBI/Primer-BLAST (ncbi.nlm.nih.gov/tools/primer-blast/). The $T_m$ of all amplicons was estimated using BioEdit software. A total of 79 primer pair were designed and screened for the standardization of this multiplex assay.

Development of Real-Time PCR Melt Curve Assay:

All primer pairs were initially screened for their specificity using DNA isolated from a standard non-O157 STEC reference set. $T_m$ was calculated for all the primers generating specific amplicons. Final primer sets for the multiplex assay were selected based on PCR product melting temperature, reaction efficiency, and product size. The multiplex assay was designed in two sets. The first set amplified *E. coli* O145, *E. coli* O121, *E. coli* O104, *E. coli* O157, and an IAC (Table 2). The second set amplified *E. coli* O26, *E. coli* O45, *E. coli* O103, *E. coli* O111, and an IAC (Table 3).

IAC Design:

A synthetic single stranded DNA sequence was designed that could be co-amplified using one of the primer pairs of the multiplex assay (generating a separate melt curve peak), and thus the IAC did not require the use of any probe for its detection. As a result, one less pair of primers was needed for the assay, which greatly reduced the complexity of the assay. The price of these custom synthesized single stranded IAC DNA is very low and they are also required in very small quantities. IAC-104121145157 (SEQ ID NO:9) and IAC-2611110345 (SEQ ID NO:18) were added to the respective multiplex assays at a concentration of 100 fg/10 µL and 10 fg/10 µL reaction, respectively.

of the PCR (from 60° C. to 95° C., with gradual temperature increments of 0.1° C./s). A melt curve plot was prepared by

TABLE 2

Primer set for the first multiplex assay

| Oligo name | SEQ ID NO | Oligo sequence | Product size (bp) | Oligo conc. | Amplicon $T_m$ (° C.) |
|---|---|---|---|---|---|
| O145-F-602 | 1 | ACTGGGATTGGACGTGGATA | 137 | 0.20 µM | 77.54 ± 0.05 |
| O145-R-738 | 2 | TCCTCCCAAAACTTCTAGGC | | 0.20 µM | |
| O121-F-716 | 3 | TGGCTAGTGGCATTCTGATG | 150 | 0.20 µM | 75.49 ± 0.06 |
| O121-R-865 | 4 | ATGCGCTTACTCCCAAGATG | | 0.20 µM | |
| O104-F-491 | 5 | CCGTAATTGAAAAGCTTGGTG | 81 | 0.20 µM | 71.45 ± 0.11 |
| O104-R-571 | 6 | CGGCTGCAAGTATCCTAAGC | | 0.20 µM | |
| O157:117-F | 7 | TTGACCCACACTTTGCCGTAA | 226 | 0.30 µM | 83.32 ± 0.07 |
| O157:117-R | 8 | GCGAAAACTGTGGAATTGGG | | 0.30 µM | |
| IAC-104121145157 | 9 | 5'-<u>TGGCTAGTGGCATTCTGATG</u>CATGGTGGCATGGGATTTTTTGCTGCAAGTGGGCTGTCCAGACAGTTCATAGTTGGTTTGGCCATATCTGTCGCATTACGAGAAACTTTCATCGTTGGTTTAACATGG<u>CATCTTGGGAGTAAGCGCAT</u>-3' | 149 | 100 fg/10 µL | 80.14 ± 0.10 |

TABLE 3

Primer set for the second multiplex assay

| Oligo name | SEQ ID NO | Oligo sequence | Product size (bp) | Oligo conc. | Amplicon $T_m$ (° C.) |
|---|---|---|---|---|---|
| O26-F-562 | 10 | TCTGGCGTGCTATCGCTTAT | 72 | 0.40 µM | 67.6 ± 0.27 |
| O26-R-633 | 11 | TTCCGCCCATTGAATTTTAG | | 0.40 µM | |
| O45-F-305 | 12 | GTCTGGCTGCAGGGACTTT | 160 | 0.07 µM | 73.4 ± 0.11 |
| O45-R-464 | 13 | AGACGAGCCTGGCTTTGATA | | 0.07 µM | |
| O103-F-752 | 14 | TAGAGGATGCCGGATATTGG | 169 | 0.07 µM | 77.09 ± 0.10 |
| O103-R-920 | 15 | GCGAGCGGTACAACAATACA | | 0.07 µM | |
| O111-F-287 | 16 | AAGGCGAGGCAACACATTAT | 85 | 0.20 µM | 81.34 ± 0.13 |
| O111-R-371 | 17 | CGATGTTGATCATCTGGGAGA | | 0.20 µM | |
| IAC-2611110345 | 18 | 5'-<u>AAGGCGAGGCAACACATTAT</u>TGACCCTGCGCTCTACCCGATAGCTGAGGCGGACTGCAGGCTGGTGGTAGCACTCAGCGCAGCGGGATGGCATCGCCACCCGCACCGGTCACCTCGACCCGAGACGCGCTCGA<u>TCTCCCAGATGATCAACATCG</u>-3' | 154 | 100 fg/10 µL | 87.35 ± 0.13 |

Real-Time PCR:

Real-time PCR assay was performed using 2× MeltDoctor HRM Master Mix (Applied Biosystems, Foster City, Calif., USA) on a StepOne Plus® real-time PCR (Applied Biosystems, Foster City, Calif., USA). Each q-PCR instrument has a fixed number of detectors, which are used to read a signal from a dual-labeled probe. In this assay, all targets were detected using a single detector (1-FAM channel). The real-time instrument was additionally calibrated for the MeltDoctor™ dye. PCR was performed in 10 µL reaction volumes in duplicate with primer concentrations provided in Tables 2 and 3. A two-step amplification protocol included an initial denaturation at 94° C. for 10 min; 40 cycles of 94° C. for 30 s, 60° C. for 45 s; and a melt curve step at the end plotting the negative derivative of fluorescence (−Rn) versus temperature. Mean $T_m$ values for each product were calculated by averaging the $T_m$ values.

The grouping of STEC serotypes in the multiplex assay was based on the frequency of occurrence of these serotypes. Among the non-O157 STEC serotypes, E. coli O26, E. coli O103, E. coli O111, and E. coli O45 are found at a much higher frequency than other serotypes (USDA, 2012). The average melting temperatures ($T_m$) of each amplicon generated in the multiplex reaction and IAC are provided in Tables 2 and 3. The assay was developed using MeltDoctor™ HRM Master Mixes containing SYTO®9, which is a high resolution saturating dye that equally intercalated to all five amplicons of the multiplex and generated a melt curve whereby all five peaks were clearly resolved (FIG. 1).

Sensitivity of the Real-Time PCR Assay:

To determine the sensitivity of the developed multiplex assay, DNA from standard cultures of STEC strains was isolated using PrepMan® Ultra Sample Preparation Reagent (Applied Biosystems, Foster City, Calif., USA). Two equal mixture DNA samples were prepared: mixture 1 contained *E. coli* O145, *E. coli* O121, *E. coli* O104, and *E. coli* O157; mixture 2 contained *E. coli* O26, *E. coli* O45, *E. coli* O103, and *E. coli* O111. These DNA mixtures were then serially diluted. One microliter of each serially diluted DNA, in triplicate, was used to determine the sensitivity of the multiplex assay.

To further validate the sensitivity of the assay, overnight cultures of STECs were serially diluted in 9 ml peptone water (1.0 g/L) and enumerated using Tryptic Soy Agar (TSA) (Difco Labs., MD, USA). DNA was isolated from 1 ml of each dilution, using the PrepMan® Ultra Sample Preparation Reagent (Applied Biosystems, Foster City, Calif., USA), and 2 µL of the obtained DNA sample was used for performing real-time PCR in a singleplex format. The obtained real-time PCR results were then correlated with bacterial count (CFU/mL) to estimate the sensitivity of the assay in singleplex.

The two multiplex assays developed in this study, when tested using equal mixtures of DNA samples, were found to work efficiently over a broad DNA concentration range. Multiplex 1, targeting *E. coli* O145, *E. coli* O121, *E. coli* O104, *E. coli* O157, and an IAC, generated positive results for all targets from 13.5 ng to 135 pg per reaction, and multiplex 2, targeting *E. coli* O26, *E. coli* O45, *E. coli* O103, *E. coli* O111, and IAC detected all targets in a DNA concentration range of 10.3 ng to 103 pg per reaction (FIG. 2). The detection limit for each primer set in singleplex format was determined using DNA isolated from decimally diluted pure broth culture and found to be between $1.4 \times 10^2$ to $4.3 \times 10^2$ pg. Corresponding Ct values obtained for each primer pair are provided in Table 4.

TABLE 4

Sensitivity of each primer in singleplex

| Bacterial Strain | Count (CFU/ml) | Ct |
|---|---|---|
| *E. coli* O26 | $4.3 \times 10^2, 1.6 \times 10^2$ | 33.8, 34.8 |
| *E. coli* O 45 | $2.6 \times 10^2, 2.2 \times 10^2$ | 34.5, 34.5 |
| *E. coli* O103 | $3.0 \times 10^2, 1.9 \times 10^2$ | 34.9, 35.6 |
| *E. coli* O111 | $1.4 \times 10^2, 1.4 \times 10^2$ | 35.4, 35.2 |
| *E. coli* O121 | $1.8 \times 10^2, 1.6 \times 10^2$ | 34.8, 34.2 |
| *E. coli* O145 | $1.7 \times 10^2, 1.5 \times 10^2$ | 34.6, 34.8 |
| *E. coli* O104 | $3.3 \times 10^2, 2.7 \times 10^2$ | 36.7, 34.0 |
| *E. coli* O157 | $1.5 \times 10^2, 1.5 \times 10^2$ | 36.0, 35.2 |

Comparison of Enrichment Media:

For the selection of suitable enrichment media for the enrichment of STECs in food samples, the applicability of three enrichment media: brain heart infusion broth (BHI) (Difco Labs., MD, USA), TSB (Difco Labs., MD, USA), and buffered peptone water (BPW) (Remel, Lenexa, Kans., USA) was tested and compared. All trials for the selection of suitable enrichment media were performed using ground beef with the highest fat content (73% lean/27% fat), which was inoculated with a cocktail of four STECs at a rate of 10 CFU (combined count of four STEC strains) per 25 g of ground beef. The effect of adding VCC supplement (Sigma-Aldrich, St. Louis, USA) on the enrichment time was also tested using the three enrichment media. Because the addition of the VCC supplement significantly slowed the growth of the STECs during enrichment, the effect of each antibiotic constituent of the VCC supplement (vancomycin [Sigma-Aldrich, St. Louis, USA], cefixime [Fluka, Sigma-Aldrich, USA], and cefsulodin [Sigma-Aldrich, St. Louis, USA]) was further investigated using BPW (Remel, Lenexa, Kans., USA) as the enrichment media.

The applicability of BHI, TSB, and BPW broths was tested for the enrichment of STECs in food samples. With ground beef (73% lean/27% fat) artificially contaminated with a cocktail of four STECs at a rate of 10 CFU, all targets of the multiplex assay were detected after an enrichment period of 6 h. The addition of VCC supplement to all three enrichment media significantly slowed the growth of STEC during the enrichment process. When the three antibiotics making up VCC supplement (e.g. vancomycin, cefixime, and cefsulodin) were individually tested for their inhibitory effect on enrichment time, vancomycin was the only antibiotic that had no adverse effects on enrichment time. Therefore, BPW with vancomycin (8 mg/lt) was selected for further studies, as it was the cheapest and most prolific media.

Preparation of Artificially Spiked Food Samples:

Ground beef of different fat contents (73% lean/27% fat, 80% lean/20% fat, 85% lean/15% fat, and 93% lean/7% fat), beef stew meat, ground chicken, ground turkey (85% Lean/15% Fat), apple cider, alfalfa sprouts, spinach, shredded iceberg lettuce, and shredded romaine lettuce were purchased from a local supermarket. Beef trims (80% lean/20% fat) were obtained from the University of Missouri (Columbia, Mo., USA) Meat Lab. To study the effect of natural microflora of each food sample on the multiplex PCR assay, aerobic plate counts of each food sample were determined using the pour plate method. The inoculum for artificially contaminating food samples was prepared by growing STEC strains in TSB overnight at 37° C. The bacterial cultures were serially diluted in 9 mL peptone water (1.0 g/L), enumerated using TSA (Difco Labs., MD, USA), and stored in the refrigerator. This method helped to achieve close to accurate inoculation levels, and the refrigeration temperature promoted stressed cells, which were more suitable for this study. The enrichment process for the spiked food samples was performed in sterile filter stomacher bags (Fisherbrand, Houston, Tex., USA). Twenty-five grams of food sample were inoculated with either of the two STEC cocktails at a rate of 10 CFU (combined count of four STEC strains). Cocktail 1 contained *E. coli* O157:H7, *E. coli* O145, *E. coli* O121, and *E. coli* O104; cocktail 2 contained *E. coli* O26, *E. coli* O45, *E. coli* O103, and *E. coli* O111. Additionally, because cefixime and cefsulodin were excluded in the enrichment broth in this study, and in order to mimic the natural microflora of meat and produce, the food samples were also spiked with $10^4$ CFU of *Pseudomonas aeruginosa* and $10^4$ CFU of *Proteus mirabilis* per 25 grams of food sample. The inoculated food samples were allowed to attach to the food matrix for 15 min at room temperature. After attachment, spiked food samples were diluted with 225 mL pre-warmed (42° C.) BPW (Remel, Lenexa, Kans., USA) containing vancomycin (8 mg/L) (Sigma-Aldrich, St. Louis, USA). A negative process control was also included in the study as described by Malorny et al. (*Internat J Food Microbiol* 117:211-218, 2007). A negative process control consisted of sterilized enrichment broth, with 25 g of food sample. The spiked food samples were stomached (Seward, London, UK) for 2 min after which it was incubated at 42±1° C. without shaking for 6 h. Each food sample for the two multiplex assays for the detection of eight STEC was processed in duplicate. After enrichment, DNA was isolated from 2 mL of enriched broth. Samples were centrifuged at 100×g for 1 min to separate suspended food particles from the media, DNA was isolated using the PrepMan® Ultra Sample Preparation Reagent (Applied Biosystems, Foster City, Calif., USA), and 1.5 µl of the obtained DNA samples were used for performing real-time PCR.

Figure 3:
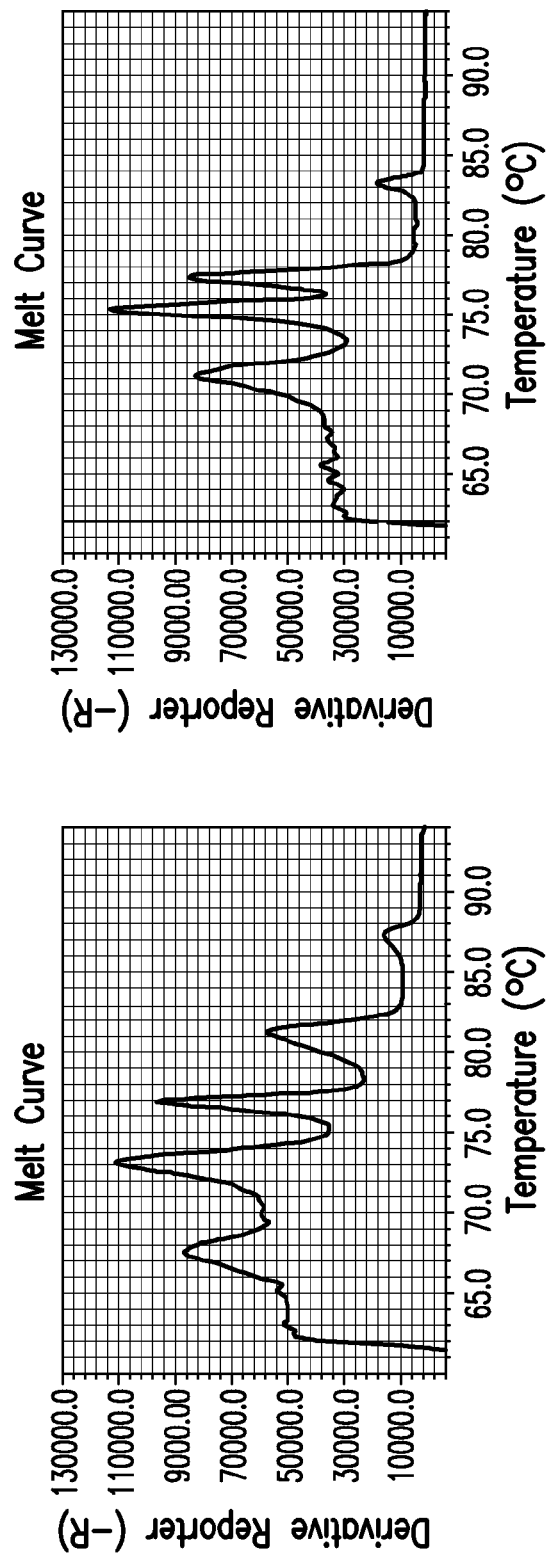
FIG. 3—Shows a melt curve obtained after real-time multiplex PCR of DNA obtained from 325 g of ground beef spiked with 10 CFU of each of eight strains of STECs enriched at 42° C.±1° C. without shaking.

Standard aerobic plate count of food samples used in this study were as follows: ground beef (96% Lean/4% Fat): $5.9 \times 10^4$ CFU/g; ground beef (85% Lean/15% Fat): $2.3 \times 10^3$ CFU/g; beef trims (80% Lean/20% Fat): $2.0 \times 10^3$ CFU/g; ground beef (73% Lean/27% Fat): $2.0 \times 10^5$ CFU/g; beef stew meat: $1.2 \times 10^4$ CFU/g; ground chicken: $9.1 \times 10^8$ CFU/g; ground turkey (85% Lean/15% Fat): $1.1 \times 10^7$ CFU/g; apple cider: <10 CFU/g; and alfalfa sprouts: $1.3 \times 10^9$ CFU/g. In all food samples inoculated with a cocktail of four STECs, (10 CFU/25 g food: combined count of four STEC strains) all targets of the multiplex assay were detected following a 6-h enrichment period (Table 5). FIG. 3 shows the melt curve obtained after real-time multiplex PCR of DNA obtained from 325 g of ground beef spiked with 10 CFU of each of eight strains of STECs enriched at 42° C.±1° C. without shaking. The IAC in each multiplex reaction formed a separate melt peak. The addition of $10^4$ CFU of *P. aeruginosa* and *P. mirabilis* to the 25 g of artificially contaminated food sample showed no negative effect on the assay. All targets of the multiplex assay were detected even in the presence of a high level of *P. aeruginosa* and *P. mirabilis*. The assay performed robustly with food samples of different fat contents, phenolic compounds, and microbial load.

TABLE 5

Real-time PCR results of 25 g food samples spiked with a cocktail of four STECs and enriched for 6 h, using BPW with vancomycin (8 mg/L) as an enrichment medium.

| Food Sample | *E. coli* O121, *E. coli* O104, *E. coli* O157, *E. coli* O145 (spiked at 10-20 CFU/25 g) | *E. coli* O26, *E. coli* O45, *E. coli* O103, *E. coli* O111 (spiked at 10-20 CFU/25 g) |
|---|---|---|
| Ground beef (96% Lean/4% Fat) | + | + |
| Ground beef (85% Lean/15% Fat) | + | + |
| Beef trims (80% Lean/20% Fat) | + | + |
| Ground beef (73% Lean/27% Fat) | + | + |
| Beef stew meat | + | + |
| Ground chicken | + | + |
| Ground turkey (85% Lean/15% Fat) | + | + |
| Apple cider | + | + |
| Alfalfa sprouts | + | + |

Spiked Food Sample Sensitivity (According to USDA Recommendation):

Using USDA recommendations, 325 g of ground beef (85% lean/15% fat) and beef trim were measured. Each was inoculated with all eight strains of STEC at concentration of 10 CFU/325 g (combined inoculum concentration of 80 CFU/325 g food sample). After inoculation, the cells were allowed to attach for 15 min at room temperature, and the samples were diluted with 975 ml of pre-warmed (42° C.) BPW (Remel, Lenexa, Kans., USA) containing vancomycin (8 mg/L) (Sigma-Aldrich, St. Louis, USA). Samples were stomached (Seward, London, UK) for 2 min and incubated for 8 h at 42° C.±1° C. without shaking. Two milliliters of enrichment broth was collected at 6 h and 8 h. DNA from the enriched broth samples was isolated as described above and diluted to (1:1) with nuclease free water. Two microliters of the obtained DNA sample was used for performing real-time PCR in both singleplex and multiplex formats. All targets of the multiplex assay were detected after an enrichment period of 8 h. The DNA samples obtained after the enrichment process were used to perform real-time PCR in both uniplex and multiplex format (FIG. 3). The obtained Ct value of each target is provided in Table 6.

TABLE 6

Mean Ct values of each PCR primer in uniplex format, inoculated with 10 CFU/325 g of ground beef.

| | | Ct | |
|---|---|---|---|
| Bacteria | Inoculum Count | 6 h | 8 h |
| *E. coli* O26 | 10 CFU, 21 CFU | 27.9, 34.2 | 27.5, 24.0 |
| *E. coli* O45 | 5 CFU, 19 CFU | 28.5, 33.4 | 22.3, 28.2 |
| *E. coli* O103 | 9 CFU, 15 CFU | 27.8, 32.2 | 22.4, 20.0 |
| *E. coli* O111 | 8 CFU, 16 CFU | 28.8, 32.3 | 23.7, 24.5 |
| *E. coli* O121 | 16 CFU, 14 CFU | 27.0, 33.7 | 21.5, 21.9 |
| *E. coli* O145 | 11 CFU, 14 CFU | 29.8, 32.7 | 21.3, 21.6 |
| *E. coli* O104 | 10 CFU, 12 CFU | 25.6, 29.4 | 18.1, 21.9 |
| *E. coli* O157 | 7 CFU, 21 CFU | UD, 34.6 | 29.8, 31.7 |

Example 2

Detection of Shiga Toxin Producing *E. coli*, Seven stx Subtypes, and *Salmonella* Via a Two-Tiered Multiplex Real-Time PCR The aim of this study was to design a two-tiered multiplex real-time PCR assay for the detection of seven Shiga toxin-producing *E. coli* (STEC) serogroups, the $stx_1$ and $stx_2$ genes, and virulent strains of *Salmonella*. DNA extraction of bacterial DNA was performed as described above.

Primer Design:

Primers were designed specific to each target STEC, stx gene, or *Salmonella* using Primer3 software. Seven STEC serogroup-specific primers were designed based on the wzx gene (Fratamico et al., *Foodborne Pathogens and Disease* 8:601-607, 2011) and the uidA gene (Cebula et al., *J Clin Microbiol* 33:248-250 1995) as described above. In addition, primers specific for Shiga toxin-producing virulence genes ($stx_1$ and $stx_2$) were designed based on conserved regions, and primers for detection of *Salmonella* were designed based on the invA gene (Rahn et al., 1996). Cultures were grown at 37° C. in tryptic soy broth, and genomic DNA was isolated.

IAC Design:

A single-stranded, 83-bp oligonucleotide was designed that could be amplified using one of the primer pairs of the multiplex assays and commercially synthesized (IDT, Coralville, Iowa United States). The optimum concentrations of each internal amplification control (IAC) oligonucleotides were separately standardized for each multiplex reaction.

Real-Time PCR:

Real-time PCR assays were performed using 2× Melt-Doctor HRM Master Mix (Applied Biosystems, Foster City, Calif., USA). The multiplex assay was standardized on a LightCycler® 96 real-time PCR (Roche Diagnostics Corp., Indianapolis, USA). The fluorescence data on the LightCycler® 96 was collected in the FAM channel of the instrument. The multiplex real-time PCR assay targeting eight pathogens and two virulence genes (7 stx subtypes) was organized in two multiplex reactions. The first reaction amplified E. coli O121, E. coli O145, E. coli O157, $stx_2$, $stx_1$, an IAC (Table 7), and the second reaction amplified E. coli O26, E. coli O111, E. coli O103, E. coli O45, *Salmonella*, and an IAC (Table 8). Real-time PCR reactions for each sample was performed in duplicate in a 10 µL reaction volume with primer concentrations mentioned in Tables 7 and 8. A two-step PCR amplification protocol included an initial denaturation at 94° C. for 10 min, and 40 cycles of 94° C. for 30 s and 60° C. for 45 s. A melt curve was performed at the end of the PCR amplification step (from 60° C. to 95° C., with gradual temperature increments of 0.04° C./s). The melt curve was plotted using the negative derivative of fluorescence (–Rn) versus temperature. Mean $T_m$ values for each amplicon was calculated by averaging the obtained $T_m$ values.

TABLE 7

Primer sets for the detection of seven Shiga toxin producing E. coli and *Salmonella*.

| Oligo name | SEQ ID NO | Oligo sequence | Product size (bp) | Primer concentration per reaction | Amplicon Tm (° C.) |
| --- | --- | --- | --- | --- | --- |
| O145-F-602 | 1 | ACTGGGATTGGACGTGGATA | 137 | 0.20 µM | 77.54 ± 0.05 |
| O145-R-738 | 2 | TCCTCCCAAAACTTCTAGGC |  | 0.20 µM |  |
| O121-F-716 | 3 | TGGCTAGTGGCATTCTGATG | 150 | 0.30 µM | 75.49 ± 0.06 |
| O121-R-865 | 4 | ATGCGCTTACTCCCAAGATG |  | 0.30 µM |  |
| O157:117-F | 7 | TTGACCCACACTTTGCCGTAA | 226 | 0.40 µM | 83.32 ± 0.07 |
| O157:117-R | 8 | GCGAAAACTGTGGAATTGGG |  | 0.40 µM |  |
| $Stx_2$-F | 19 | TACCACTCTGCAACGTGTCG | 164 | 0.12 µM | 81.5 ± 0.2 |
| $Stx_2$-R | 20 | AGGCTTCTGCTGTGACAGTG |  | 0.12 µM |  |
| $Stx_1$-F | 21 | ATCGCTTTRCTGATTTTTCA | 56 | 0.40 µM | 73.8 ± 0.2 |
| $Stx_1$-R | 22 | CAATGTAACCGCWSTTGTACC |  | 0.40 µM |  |
| IAC-O157-set-121pp | 23 | CATATATGGCTAGTGGCATTC TGATGATATATATATTATCAA AATAAGACTAATAAAGCATCT TGGGAGTAAGCGCATCATAC | 72 | 20 fg/10 µL | 70.56 ± 0.05 |

TABLE 8

Primer sets for the detection of seven Shiga toxin producing E. coli and *Salmonella*.

| Oligo name | SEQ ID NO | Oligo sequence | Product size (bp) | Primer concentration per reaction | Amplicon Tm (° C.) |
| --- | --- | --- | --- | --- | --- |
| O26-F-999 | 24 | AAGCGCGTTCATCCCTTTAT | 83 | 0.25 µM | 72.2 ± 0.07 |
| O26-R-1081 | 25 | ACAATCCAACCGAACCAAAC |  | 0.25 µM |  |
| O45-F-317 | 26 | GGACTTTCGTTGCGTTGTG | 142 | 0.10 µM | 80.9 ± 0.1 |
| O45-R-458 | 27 | GCCTGGCTTTGATACCATGT |  | 0.10 µM |  |
| O103-F-752 | 14 | TAGAGGATGCCGGATATTGG | 169 | 0.25 µM | 77.8 ± 0.09 |
| O103-R-920 | 15 | GCGAGCGGTACAACAATACA |  | 0.25 µM |  |
| O111-F-287 | 16 | AAGGCGAGGCAACACATTAT | 72 | 0.10 µM | 75.1 ± 0.1 |
| O111-R-385 | 28 | GCCAAAGGTATTCACGATGTT |  | 0.10 µM |  |
| *Salmonella*-F | 29 | CGGTGGGTTTTGTTGTCTTC | 237 | 0.10 µM | 83.3 ± 0.05 |
| *Salmonella*-R | 30 | TCATCGCACCGTCAAAGGA |  | 0.10 µM |  |

TABLE 8-continued

Primer sets for the detection of seven Shiga toxin producing E. coli and Salmonella.

| Oligo name | SEQ ID NO | Oligo sequence | Product size (bp) | Primer concentration per reaction | Amplicon Tm (° C.) |
|---|---|---|---|---|---|
| IAC-Sal-set-103pp | 31 | CATATA<u>TAGAGGATGCCGGAT</u> <u>ATTGG</u>ATATATATATTATCAAA ATAAGACTAATAAAG<u>TGTATT</u> <u>GTTGTACCGCTCGCCATAC</u> | 72 | 10 fg/10 μL | 69.7 ± 0.05 |

Specificity of Shiga Toxin Gene Primers:

The conserved Shiga toxin gene primers designed in this study were evaluated for their ability to amplify various stx subtypes. Reference DNA samples of various $stx_1$ and $stx_2$ subtypes were generously donated by Dr. Peter C. H. Feng (FDA, College Park, Md.) (Feng et al., *Appl Environ Microbiol* 77:6699-6702, 2011).

Spiked Food Sample Sensitivity (According to USDA Recommendation):

Ground beef and beef trims were obtained from the University of Missouri Meat Lab (Columbia, Mo., USA). Three hundred and twenty five grams of ground beef and beef trim were measured in stomacher bags, according to USDA recommendations (MLG 5B.05). Each beef sample was inoculated with all seven STECs serogroups and *Salmonella* at individual concentrations of 10 CFU/325 g (combined inoculum concentration of all eight pathogens≈80 CFU/325 g food sample). To verify the robustness of the assays, in addition to the eight pathogens (seven STEC serogroups and *Salmonella*), the food samples were also spiked with $10^4$ CFU of *Pseudomonas aeruginosa* and $10^4$ CFU of *Proteus mirabilis* per 325 g of samples. After inoculation, the cells were allowed to attach for 15 min at room temperature. In order to mimic the beef processing plant scenario, the inoculated beef samples were refrigerated at 4° C. for 72 h to stress the pathogens. Then, the beef samples were diluted with 975 mL of pre-warmed (42° C.) BPW (Remel, Lenexa, Kans., USA) containing vancomycin (8 mg/L) (Sigma-Aldrich, St. Louis, USA). Ground beef samples were stomached (Seward, London, UK) for 2 min while the beef trims were hand-massaged and incubated for 10 h at 40° C.±2° C. without shaking. A negative process control as described by Malorny et al. (*Internat J Food Microbiol* 117:211-218, 2007) was also included in the study. A negative process control consisted of sterilized enrichment broth (BPW) with 325 g of beef sample. Two milliliters of enrichment broth were collected at 8 h and 10 h. DNA from the enrichment broth was isolated using PrepMan® Ultra Sample Preparation Reagent. The obtained DNA was diluted to a concentration of 75 ng/μL with nuclease-free water. One hundred to 150 ng of this diluted DNA sample was used for performing real-time PCR as described above. The assay with all the strains used in this study was repeated twice using beef of different fat contents.

Results:

The real-time PCR assay was standardized using equal concentration mixtures of pure DNA samples. The multiplex assays developed in this study, targeting a total of 15 genes and an IAC were organized in two reactions. Among 7 STEC serogroups declared as adulterants in non-intact beef, *E. coli* O157 has highest frequency of occurrence (Dewsbury et al., *Foodborne Pathogens and Disease,* 2015; Stromberg et al., *Foodborne Pathogens and Disease* 12(7):631-638, 2015).

Further, identification of STEC virulence genes ($stx_1$, $stx_2$) is considered to be essential for the identification of virulent strains of STEC (13). Hence, the first multiplex reaction was designed to target *E. coli* O157, $stx_1$, $stx_2$ and two other non-O157 STEC serogroups. Among the non-O157 STECs, *E. coli* O26, *E. coli* O103, and *E. coli* O111 are found at a much higher frequency than the other serogroups. The second multiplex can be used for the detection of most commonly found non-O157 STEC serogroups. An IAC was added to both multiplex PCR reactions to prevent any false-negative results (FIG. 4A, 4B). The IAC concentrations were individually standardized for each multiplex reaction, IAC-O157-set-121pp (SEQ ID NO:23) and IAC-Sal-set-103pp (SEQ ID NO:31) were used at a concentration of 20 fg and 10 fg per 10 μL reaction volume, respectively. The two conserved stx primers designed in this study were able to detect seven stx subtypes. The $stx_1$ primer pair amplified $stx_{1a}$, $stx_{1c}$ and $stx_{1d}$ subtypes, whereas the $stx_2$ primers targeted $stx_{2a}$, $stx_{2c}$, $stx_{2d}$, and $stx_{2e}$ subtypes.

A sample size of 325 g of ground beef and beef trims were used for the validation of real-time PCR in this study. Fat is one of the major PCR inhibitors. Hence, for the validation of the assay, all strains under study were initially tested using beef samples with 20% fat and the results were further revalidated using beef samples with 10% fat contents. The inoculum count of all STEC strains used in this study ranged between 5-27 CFU/325 g beef, whereas the inoculum count of *Salmonella* strains used were 9-36 CFU/325 g beef. Irrespective of fat content of beef samples, STEC strains used in this study could be detected after an 8-10 h enrichment period. A longer enrichment time of 10 h was required for beef samples with higher microflora count. Out of all the STEC strains tested, the results of spiked food samples for four STEC strains (*E. coli* O145:H NT-IH 16, *E. coli* O121 PT91-4, *E. coli* O121 5518 and *E. coli* O26 TB285C) were not reproducible. Growth of these four strains was affected by two factors: the initial microflora count of the beef and the inoculum concentration used to spike the beef samples. Because the beef samples were inoculated as a cocktail of eight pathogens (seven STEC strains and one *Salmonella*), this led to competition among strains for the same nutrients. When these four strains were individually inoculated (not as a cocktail of eight pathogens) in 325 g of beef, each strain was reliably detected after an 8 h of enrichment time, indicating that these four strains are poor competitors and were outpaced by high beef microflora, other STEC strains or *Salmonella* strains.

The reproducibility of the assay was validated using 55 STEC strains belonging to 7 serogroups and 8 strains of *Salmonella* (Table 9) using 325 g of ground beef and beef trims of different fat contents. A 325-g sample of ground beef was spiked with 10 CFU of each of the seven STECs and one *Salmonella* species at 10 CFU of each pathogen/325 g (combined inoculum of 80 CFU/325 g). Spiked beef was stored at 4° C. for 72 h. The pathogens introduced to the beef samples were able to be detected after an enrichment period of 10 h. The assay generated consistent results for beef samples with 10% and 20% fat. The assay is recommended for testing food samples with low to moderate level microflora. Samples with high microflora may require a longer enrichment time.

TABLE 9

Strains Used in Validation of Assay.

| STEC Strain | Origin | | (CFU/325 g) | Enrichment |
|---|---|---|---|---|
| E. coli O157:H7 | 3178-85 | Human | 10, 14 | 8 |
| E. coli O157:H7 | C7927 | Human | 14, 15 | 8 |
| E. coli O157 | 93-111 | Human | 15, 13 | 8 |
| E. coli O157 | EDL-933 | Hamburger | 7, 13 | 8 |
| E. coli O157 | OK-1 | Human | 19, 7 | 8 |
| E. coli O157 | 2886-75 | Human | 18, 9 | 8 |
| E. coli O157 | 86-24 | Human | 8, 10 | 8 |
| E. coli O157 | G5101 | Human | 14, 11 | 8 |
| E. coli O26:H11 | DEC10B | Human | 21, 15 | 8 |
| E. coli O26:H | MT#10 | Human | 8, 16 | 8 |
| E. coli O26 | H19 | Human | 7, 9 | 8 |
| E. coli O26 | DEC10C | Human | 7, 12 | 8 |
| E. coli O26 | DEC9F | Human | 15, 5 | 8 |
| E. coli O26 | TB285C | Human | 12, 13 | 8-10 |
| E. coli O26 | VP30 | Human | 12, 10 | 8 |
| E. coli O26 | DEC9A | Human | 13, 10 | 8 |
| E. coli O45:H2 | M103-19 | Human | 13, 27 | 8 |
| E. coli O45:H NM | DA-21 | Human | 11, 11 | 8 |
| E. coli O45 | DEC11C | Human | 9, 5 | 8 |
| E. coli O45 | 5431-72 | Human | 10, 12 | 8 |
| E. coli O45 | 4309-65 | Human | 12, 13 | 8 |
| E. coli O45 | 88-4110-H | Cow | 11, 10 | 8 |
| E. coli O45 | D88-28058 | Cow | 11, 12 | 8 |
| E. coli O45 | 2566-58 | Pig | 12, 12 | 8 |
| E. coli O103:H2 | MT#80 | Human | 13, 12 | 8 |
| E. coli O103:H N | PT91-24 | Human | 17, 18 | 8 |
| E. coli O103 | DA-41 | Human | 9, 13 | 8 |
| E. coli O103 | 6:38 | Human | 11, 9 | 8 |
| E. coli O103 | PT91-24 | Human | 18, 5 | 8 |
| E. coli O103 | DA-55 | Human | 12, 5 | 8 |
| E. coli O103 | 87-2931 | Human | 10, 14 | 8 |
| E. coli O103 | GS G5550637 | Human | 12, 11 | 8 |
| E. coli O111:H2 | RD8 | Human | 13, 23 | 8 |
| E. coli O111:H NM | 3007-85 | Human | 12, 14 | 8 |
| E. coli O111 | CL-37 | Human | 11, 7 | 8 |
| E. coli O111 | DEC8B | Human | 10, 9 | 8 |
| E. coli O111 | TB226A | Human | 17, 6 | 8 |
| E. coli O111 | 928/91 | Human | 12, 11 | 8 |
| E. coli O111 | 412/55 | Human | 13, 14 | 8 |
| E. coli O111 | DEC8C | Cow | 8, 13 | 8 |
| E. coli O121:H[19] | DA-5 | Human | 11, 16 | 8 |
| E. coli O121 | 87-2914 | Human | 14, 6 | 8 |
| E. coli O121 | DA-1 | Human | 6, 11 | 8 |
| E. coli O121 | 7927+++ | | 20, 13 | 8 |
| E. coli O121 | 5518 | | 12, 10 | 8-10 |
| E. coli O121 | O121 standard | | 14, 17 | 8 |
| E. coli O121 | PT91-4 | | 13, 15 | 8-10 |
| E. coli O145:H NT | D177 | Human | 14, 13 | 8 |
| E. coli O145:H NT | IH 16 | Human | 14, 16 | 8-10 |
| E. coli O145 | 70300885 | | 9, 10 | 8 |
| E. coli O145 | MT#66 | Human | 9, 12 | 8 |
| E. coli O145 | 6940 | | 16, 6 | 8 |
| E. coli O145 | BCL73 | Cow | 8, 15 | 8 |
| E. coli O145 | B6820-C1 | Cow | 8, 11 | 8 |
| Salmonella Agona | LJH1132 | | 15, 36 | 8 |
| Salmonella Agona | LJH1122 | | 24, 13 | 8 |
| Salmonella Newport | LJH692 | | 18, 13 | 8 |
| Salmonella Typhimurium | 14028 | | 20, 19 | 8 |
| Salmonella Typhimurium | 788 | | 26, 15 | 8 |
| Salmonella Typhimurium | LJH666 | | 9, 17 | 8 |
| Salmonella Thompson | B&B3 | | 20, 17 | 8 |
| Salmonella Enteritidis | | | 14, 10 | 8 |

The assays described herein detected all three $stx_1$ subtypes ($stx_{1a}$, $stx_{1c}$, and $stx_{1d}$) and four $stx_2$ subtypes ($stx_{2a}$, $stx_{2c}$, $stx_{2d}$, and $stx_{2e}$), which include all the important $stx_2$ subtypes that are most commonly associated with HUS cases. Unlike, other commercial Shiga toxin detection assays (Assurance GDS STEC, BAX System STEC Suite Screening, iQ Check STEC VirX, GeneDisc STEC, and E. coli O157, ABI Custom TaqMan® VT1/VT2 assays) that require special instruments and analytical software for performing the assay, the assays of the present invention, which can be performed using any real-time PCR instrument, also detect STEC serogroup-specific genes in addition to important stx genes and Salmonella.

The assays developed in this study are effective and low cost assays for the screening of E. coli O157, non-O157 STEC, STEC virulence genes and Salmonella in non-intact beef samples. This assay also meets the recent USDA FSIS guidelines for Salmonella testing and will be a useful tool for simultaneous screening of STEC and Salmonella in non-intact beef samples. In addition, the assays can be completed in less than 11 h, making them highly suitable for industrial application.

Example 3

Multiplex Real-Time PCR Assay for the Detection of Extended-Spectrum β-Lactamase (ESBL) and Carbapenemase Genes Using Melting Curve Analysis Screening for ESBL or carbapenemase producing Enterobacteriaceae is generally performed using commercially available selective agar plates. Standard microbiological procedures can take up to several days for the culture, isolation and characterization of antibiotic resistance profile of pathogens from a sample. The total time required for this process can add up to 4-6 days for getting an accurate antimicrobial susceptibility test results (Lupo et al., Diagnostic microbiology and infectious disease 77:179-194, 2013). However, many recent comparative studies have shown that commercially available selective agars have lower sensitivity than PCR-based methods (Naas et al., Antimicrob Agents Chemother 55:4038-4043, 2011; Singh et al., J Clin Microbiol 50:2596-2600, 2012), due to variable levels of expression of ESBL and carbapenemase genes. Therefore, the objective of this study was to develop a real-time PCR melt curve assay for the detection of extended-spectrum β-lactamase (ESBL) and carbapenemase producing Gram-negative pathogens.

Two multiplex real-time PCR melt curve assays were standardized for the detection of 10 most common resistance genes: $bla_{KPC-like}$, $bla_{NDM-like}$, $bla_{CTX-M-1/2-group}$, $bla_{CMY-like}$, $bla_{ACC-like}$, $bla_{VIM-like}$, $bla_{IMP-like}$, $bla_{OXA-48-like}$, $bla_{SHV-like}$, and $bla_{TEM-like}$. The multiplex was evaluated using a total of 56 DNA samples comprising different genera of Enterobacteriaceae and *Pseudomonas*, which were obtained from five research institutes. The assay developed in this study offers a simple, low cost method for the detection of ESBL and carbapenemase genes among Gram-negative pathogens.

Bacterial Strains and DNA Extraction:

Bacterial strains (n=25) and DNA samples (n=31) of β-lactam-resistant isolates of *Salmonella* and other Enterobacteriaceae were obtained from the Robert Koch Institute, (Berlin, Germany), Calgary Laboratory Services, (Calgary, AB, Canada), Institute of Microbiology, University of Lausanne and University Hospital Center, (Lausanne, Switzerland), bioMérieux (St. Louis, Mo., USA), and University Hospital, University of Missouri (Columbia, Mo., USA). The β-lactamase production and identification of β-lactamase types was previously performed by different methods (standard PCR and gene sequencing, and MALDI-TOF) in these five facilities. Genomic DNA from all bacterial isolates used in this study was isolated using PrepMan® Ultra Sample Preparation Reagent (Applied Biosystems, Foster City, Calif., USA) according to the manufacturer's instructions. The concentrations and purity of the obtained DNA samples was determined using a Nanodrop 2000 spectrophotometer (Thermo Fisher Scientific, Wilmington, Del., USA).

Primer Design:

A total of 85 primer pairs targeting 10 antibiotic resistance genes ($bla_{KPC-like}$, $bla_{NDM-like}$, $bla_{CTX-M-1/2-group}$, $bla_{CMY-like}$, $bla_{TEM-like}$, $bla_{ACC-like}$) were designed and evaluated for the standardization of the multiplex real-time PCR melt curve assay. The primers were designed such as to keep the melting temperature ($T_m$) of the PCR amplicons between 67° C. to 87° C. and each amplicon's $T_m$ separated from a neighboring amplicon's $T_m$ by approximately 2-3° C. The specificity of the designed PCR primers was tested using NCBI/Primer-BLAST. The designed oligonucleotides were commercially synthesized (IDT, Coraville, Iowa, USA). PCR amplification conditions for each primer pair were standardized using conventional gradient PCR. Real-time PCR was performed using MeltDoctor™ HRM master mix (Applied Biosystems, Foster City, Calif., USA) in singleplex format for the estimation of the $T_m$ of each PCR amplicon. Based on the obtained $T_m$ values of the amplicons in singleplex reactions, a multiplex real-time melt curve assay was standardized in a stepwise manner. PCR primers generating low $T_m$ amplicons (e.g., 70° C.) were tested for their ability to work in a multiplex reaction with primer-pairs of another gene generating amplicons of $T_m$ values 2-3° C. higher and subsequently targeting primers with higher amplicon $T_m$ in a step-wise manner.

IAC Design:

Two reaction-specific, single-stranded, 75-100 base long DNA sequences were designed to act as the IAC in the multiplex real-time PCR reaction. These IAC molecules could be amplified using one of the primer pairs of the multiplex assay (but generating a separate melt curve peak). The IAC concentrations of each multiplex assay was optimized and kept as low as possible to prevent any possible competition for primers and facilitating the preferential amplification of the antibiotic resistance genes.

Real-Time PCR:

All primers generating specific amplicons in the conventional PCR and real-time PCR reactions were tested for their suitability for the development of the multiplex real-time melt curve assay. The final primer sets for the assay were selected based on PCR reaction efficiency around 90% or higher in singleplex reactions, a minimum of 2-3° C. difference in melting temperature between neighboring peaks to allow for greater resolution between melting peaks and to avoid any overlap of melting peaks, with amplicon sizes between 51-250 bp. The diversity of the family of β-lactamase enzymes is very high. In addition, each family of enzymes comprises hundreds of allelic variants of the specific gene. Primer-BLAST was performed for each of the primer-pairs used in this study to find allelic variants that possessed similar primer binding sites.

The multiplex assay for the detection of ESBL and carbapenemase producing bacteria was designed in two sets. The first set included five primer-pairs for the amplification of $bla_{KPC-like}$, $bla_{NDM-like}$, $bla_{CTX-M-1/2group}$, $bla_{CMY-like}$, and $bla_{VIM-like}$ genes with an IAC (Table 10). The second set targeted $bla_{IMP-like}$, $bla_{OXA-like}$, $bla_{SHV-like}$, $bla_{TEM-like}$ and $bla_{ACC-like}$ antibiotic resistant genes and IAC (Table 11). Real-time PCR assay was performed in a 15 μL reaction volume with 2× MeltDoctor™ HRM master mix (Applied Biosystems, Foster City, Calif., USA). A touchdown PCR amplification protocol was used in a LightCycler® 96 real-time PCR platform (Roche Diagnostics Corporation, Indianapolis, USA). The PCR program for the amplification consisted of the following steps: 10 min of initial denaturation step at 95° C. followed by 40 cycles of denaturation at 95° C. for 10 s, initial annealing at 65° C. for 40 s (gradual temperature decrements of 0.2° C. per cycle, final annealing temperature 60° C.), extension and data collection at 72° C. for 10 s. Melting of amplicons was performed at 0.04° C./s (25 reading/° C.).

TABLE 10

Primer set for the first multiplex assay.

| Oligo | SEQ ID NO | Oligo Sequence | Oligo conc. | Product size (bp) | Amplicon $T_m$ (° C.) |
|---|---|---|---|---|---|
| KPC-688-F | 32 | GTCGGAGACAAAACCGGAAC | 0.26 μM | 51 | 77.8 |
| KPC-738-R | 33 | ATAGTCATTTGCCGTGCCATA | 0.26 μM | | |
| NDM-310-F | 34 | TGGATCAAGCAGGAGATCAA | 0.26 μM | 250 | 88.4 |
| NDM-559-R | 35 | GGCCGGGGTAAAATACCTT | 0.26 μM | | |
| CTX-583-F | 36 | AATCTGACGCTGGGTAAAG | 0.16 μM | 140 | 85.5 |
| CTX-722-R | 37 | CCGCTGCCGGTTTTATC | 0.16 μM | | |
| CMY-55-F | 38 | GTTCAGGAGAAAACGCTCCA | 0.2 μM | 87 | 82.2 |

TABLE 10-continued

Primer set for the first multiplex assay.

| Oligo | SEQ ID NO | Oligo Sequence | Oligo conc. | Product size (bp) | Amplicon $T_m$ (° C.) |
|---|---|---|---|---|---|
| CMY-141-R | 39 | CCAGCCTAATCCCTGGTACA | 0.2 µM | | |
| VIM-215-F | 40 | TCATTGTCCGTGATGGTGAT | 0.26 µM | 51 | 74.4 |
| VIM-265-R | 41 | CACCCCACGCTGTATCAATC | 0.26 µM | | |
| IAC-NDM-pp | 42 | catataTGGATCAAGCAGGAGATCAAT ATATATATTATCAAAATAAGACTAAT AAAGAAGGTATTTTACCCCGGCCcatac | 10 fg/15 µl | 71 | 69 |

TABLE 11

Primer set for the second multiplex assay.

| Oligo | SEQ ID NO | Oligo Sequence | Oligo conc. | Product size (bp) | Amplicon $T_m$ (° C.) |
|---|---|---|---|---|---|
| IMP-311-F | 43 | TAGAGTGGCTTAATTCTCRATC | 0.16 µM | 75 | 77.8 |
| IMP-577-R | 44 | CTTCTAWATTTGCGTCACCC | 0.16 µM | | |
| OXA48-63-F | 45 | AGCAAAGGAATGGCAAGAAA | 0.23 µM | 65 | 73.6 |
| OXA48-127-R | 46 | CGCCCTGTGATTTATGTTCA | 0.23 µM | | |
| SHV-309-F | 47 | GGTCAGCGAAAAACAYCTTG | 0.4 µM | 195 | 88.2 |
| SHV-503-R | 48 | GCCTCATTCAGTTCCGTTTC | 0.4 µM | | |
| TEM-94-F | 49 | GATACGGGAGGGCTTACCAT | 0.2 µM | 146 | 85.0 |
| TEM-239-R | 50 | GGATGGAGGCGGATAAAGTT | 0.2 µM | | |
| ACC-238-F | 51 | GAGCAAATTCGGCAGAGAAA | 0.2 µM | 115 | 81.6 |
| ACC-352-R | 52 | CAAGATGCAACAGGCTCTGA | 0.2 µM | | |
| IAC-SHV-pp | 53 | catataGGTCAGCGAAAAACAYCTTGAT ATATATATTATCAAAATAAGACTAAT AAAGGAAACGGAACTGAATGAGGCcatac | 10 fg/15 µl | 72 | 70 |

Results:

Conserved primer pairs were designed for the multiplex real-time PCR assays to amplify the dominant as well as other less commonly or geographically restricted allelic variants. The primer-BLAST results showed that, in addition to dominant allelic variants, the primer pairs were capable of amplifying a vast number of allelic variants that are commonly found among members of the Enterobacteriaceae (Table 12).

Figure 5A:
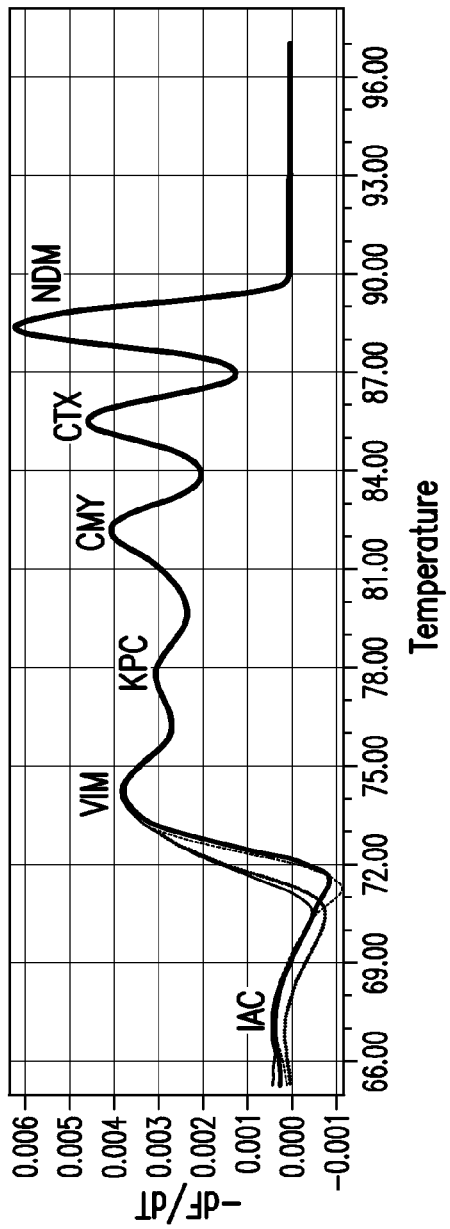
FIGS. 5A-5B—Shows a melt curve for a multiplex assay for the detection of: $bla_{KPC-like}$, $bla_{NDM-like}$, $bla_{CTX-M-1/2group}$, $bla_{CMY-like}$, and $bla_{VIM-like}$ genes, with an IAC (FIG. 5A); and Non-template control sample showing the IAC melt peak for the multiplex assay reaction (FIG. 5B).
Figure 5B:
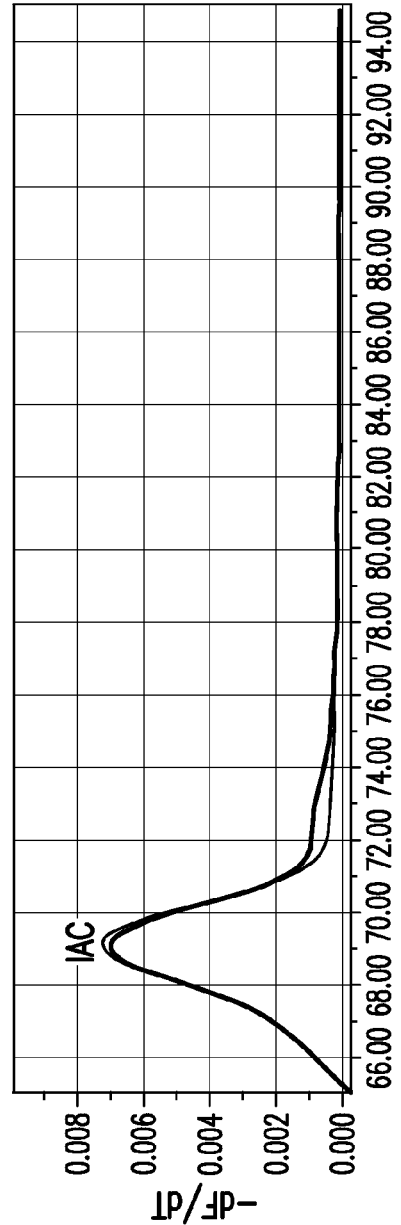

Two multiplex real-time PCR reactions were developed for the identification of 10 genes, coding for ESBLs and carbapenemase enzymes. The first set targeted $bla_{KPC-like}$, $bla_{NDM-like}$, $bla_{CTX-M-1/2-group}$, $bla_{CMY-like}$, $bla_{VIM-like}$ genes and IAC (FIG. 5). The IAC molecule (IAC-SEQ ID NO:42) in this reaction was amplified using the primer pairs, NDM-310-F (SEQ ID NO:34) and NDM-559-R (SEQ ID NO:35), generating a separate melting peak at 69° C. Because two targets ($bla_{NDM}$ and IAC) were simultaneously amplified using one primer pair, the IAC molecule was added at a very low concentration (10 pg/15 µL reaction) in order to allow preferential amplification of the target DNA (instead of the IAC). As a result, the melt peak formed by the IAC amplicon was much smaller than the other peaks of the multiplex assay (FIG. 5A). However, in the absence of the NDM target or in the non-template control (NTC), a bigger IAC melt peak was observed (FIG. 5B). The second multiplex reaction targeted $bla_{IMP-like}$, $bla_{OXA-like}$, $bla_{SHV-like}$, $bla_{TEM-like}$, $bla_{ACC-like}$ and the IAC (FIG. 6A). In this multiplex reaction, the IAC molecule (IAC-SHV-pp, SEQ ID NO:53) was co-amplified by SHV-309-F (SEQ ID NO:47) and SHV-503-R (SEQ ID NO:48) primer-pairs and the IAC amplicon generated a separate melt peak at 70° C. (FIG. 6B).

The result of the multiplex PCR assay mostly concurred with ESBL and carbapenemase genes that were detected in previous studies (Table 13). In addition to the previously reported antibiotic resistant (ABR) determinants, this multiplex assay was also able to detect the presence of a few other ABR genes (Table 13). Salmonella enterica Newport 209/10 and Escherichia coli 2/10, were previously reported as positive for $bla_{CTX-M-8}$ and $bla_{OXA-1/2}$ respectively. However, these genes could not be detected using this multiplex assay. This might be due to the high allelic diversity within each antibiotic-hydrolyzing enzyme family.

In another comparative study, DNA samples obtained from the Institute of Microbiology, University of Lausanne and University Hospital Center (Lausanne, Switzerland) was evaluated using this multiplex assay. In a previous study, these isolates were evaluated using MALDI-TOF and the presence of resistance genes were confirmed using Check-MDR Carba and Check-MDR CT103 microarray kits for the presence of β-lactamases (Vogne et al., *Clin Microbiol Infect* 20:01106-01112, 2014). The multiplex assay developed in this current study worked equally well for all strains except for a KPC-positive *Serratia marcescens* 8057 isolate. Additionally, with this assay, the presence of other β-lactamase genes was also identified in many of these strains (Table 13).

Similar results were obtained for the DNA samples received from bioMérieux (Table 13). Additional β-lactamase genes were detected using the multiplex assay developed in this study, which were later confirmed by sequencing. *E. coli* 104039 strain that was reported to carry TEM-1 and TEM-4 genes generated a wide peak in the melt curve plot. This wide peak was most probably formed by the merger of two very close peaks, which was generated by the amplification of two $bla_{TEM}$ genes (TEM-1 and TEM-4) present in this DNA sample. Similarly *P. aeruginosa* 111615 strains also generated two very close peaks (76.7° C., 78.4° C.) in the melt curve plot. These two peaks were very close to the standard IMP peak (77.8° C.) obtained in this study. The presence of two peaks in a melt curve plot suggests the possibility of two IMP alleles in the sample. However, the assay failed to detect the presence of NDM gene in *K. pneumonia* 115415.

Therefore, this study demonstrates a multiplex real-time melt curve PCR assay that can be used for the simultaneous detection of 10 most frequently and globally occurring β-lactamase genes of Gram-negative bacteria that confer resistance to various cephalosporins and carbapenems. This assay is suitable for use by regulatory agencies for conducting routine surveillance of antibiotic resistant foodborne pathogens.

TABLE 12

Allelic variants with the same primer-binding site.

| Gene | SEQ ID NO | Primer sequence | Detectable allelic variants |
|---|---|---|---|
| $bla_{KPC}$ | 32<br>33 | GTCGGAGACAAAACCGGAAC<br>ATAGTCATTTGCCGTGCCATA | $bla_{KPC-2}$, $bla_{KPC-3}$, $bla_{KPC-4}$, $bla_{KPC-5}$, $bla_{KPC-6}$, $bla_{KPC-7}$, $bla_{KPC-8}$, $bla_{KPC-9}$, $bla_{KPC-11}$, $bla_{KPC-15}$, $bla_{KPC-16}$, $bla_{KPC-17}$, $bla_{KPC-19}$ |
| $bla_{NDM}$ | 34<br>35 | TGGATCAAGCAGGAGATCAA<br>GGCCGGGGTAAAATACCTT | $bla_{NDM-1}$, $bla_{NDM-3}$, $bla_{NDM-4}$, $bla_{NDM-5}$, $bla_{NDM-6}$, $bla_{NDM-7}$, $bla_{NDM-8}$, $bla_{NDM-9}$, $bla_{NDM-10}$, $bla_{NDM-12}$ |
| $bla_{CTX}$ | 36<br>37 | AATCTGACGCTGGGTAAAG<br>CCGCTGCCGGTTTTATC | $bla_{CTX-M-1}$, $bla_{CTX-M-2}$, $bla_{CTX-M-3}$, $bla_{CTX-M-4}$, $bla_{CTX-M-5}$, $bla_{CTX-M-12}$, $bla_{CTX-M-15}$, $bla_{CTX-M-22}$, $bla_{CTX-M-29}$, $bla_{CTX-M-32}$, $bla_{CTX-M-28}$, $bla_{CTX-M-30}$, $bla_{CTX-M-31}$, $bla_{CTX-M-34}$, $bla_{CTX-M-35}$, $bla_{CTX-M-36}$, $bla_{CTX-M-37}$, $bla_{CTX-M-44}$, $bla_{CTX-M-54}$, $bla_{CTX-M-55}$, $bla_{CTX-M-56}$, $bla_{CTX-M-57}$, $bla_{CTX-M-58}$, $bla_{CTX-M-59}$, $bla_{CTX-M-61}$, $bla_{CTX-M-66}$, $bla_{CTX-M-68}$, $bla_{CTX-M-69}$, $bla_{CTX-M-71}$, $bla_{CTX-M-79}$, $bla_{CTX-M-82}$, $bla_{CTX-M-89}$, $bla_{CTX-M-101}$, $bla_{CTX-M-103}$, $bla_{CTX-M-108}$, $bla_{CTX-M-109}$, $bla_{CTX-M-114}$, $bla_{CTX-M-116}$, $bla_{CTX-M-117}$, $bla_{CTX-M-131}$, $bla_{CTX-M-132}$, $bla_{CTX-M-136}$, $bla_{CTX-M-137}$, $bla_{CTX-M-141}$, $bla_{CTX-M-142}$, $bla_{CTX-M-144}$ |
| $bla_{CMY}$ | 38<br>39 | GTTCAGGAGAAAACGCTCCA<br>CCAGCCTAATCCCTGGTACA | $bla_{CMY-2}$, $bla_{CMY-4}$, $bla_{CMY-6}$, $bla_{CMY-7}$, $bla_{CMY-12}$, $bla_{CMY-14}$, $bla_{CMY-15}$, $bla_{CMY-16}$, $bla_{CMY-18}$, $bla_{CMY-21}$, $bla_{CMY-22}$, $bla_{CMY-23}$, $bla_{CMY-25}$, $bla_{CMY-26}$, $bla_{CMY-27}$, $bla_{CMY-28}$, $bla_{CMY-29}$, $bla_{CMY-30}$, $bla_{CMY-31}$, $bla_{CMY-32}$, $bla_{CMY-33}$, $bla_{CMY-37}$, $bla_{CMY-38}$, $bla_{CMY-39}$, $bla_{CMY-40}$, $bla_{CMY-41}$, $bla_{CMY-42}$, $bla_{CMY-43}$, $bla_{CMY-45}$, $bla_{CMY-46}$, $bla_{CMY-47}$, $bla_{CMY-48}$, $bla_{CMY-49}$, $bla_{CMY-50}$, $bla_{CMY-51}$, $bla_{CMY-53}$, $bla_{CMY-54}$, $bla_{CMY-55}$, $bla_{CMY-56}$, $bla_{CMY-57}$, $bla_{CMY-58}$, $bla_{CMY-59}$, $bla_{CMY-60}$, $bla_{CMY-61}$, $bla_{CMY-62}$, $bla_{CMY-63}$, $bla_{CMY-64}$, $bla_{CMY-65}$, $bla_{CMY-66}$, $bla_{CMY-67}$, $bla_{CMY-68}$, $bla_{CMY-69}$, $bla_{CMY-71}$, $bla_{CMY-72}$, $bla_{CMY-73}$, $bla_{CMY-75}$, $bla_{CMY-77}$, $bla_{CMY-78}$, $bla_{CMY-79}$, $bla_{CMY-80}$, $bla_{CMY-81}$, $bla_{CMY-84}$, $bla_{CMY-85}$, $bla_{CMY-86}$, $bla_{CMY-87}$, $bla_{CMY-90}$, $bla_{CMY-96}$, $bla_{CMY-97}$, $bla_{CMY-99}$, $bla_{CMY-102}$, $bla_{CMY-104}$, $bla_{CMY-105}$, $bla_{CMY-108}$, $bla_{CMY-110}$, $bla_{CMY-111}$ |
| $bla_{VIM}$ | 40<br>41 | TCATTGTCCGTGATGGTGAT<br>CACCCCACGCTGTATCAATC | $bla_{VIM-1}$, $bla_{VIM-2}$, $bla_{VIM-4}$, $bla_{VIM-5}$, $bla_{VIM-19}$, $bla_{VIM-23}$, $bla_{VIM-24}$, $bla_{VIM-25}$, $bla_{VIM-27}$, $bla_{VIM-31}$, $bla_{VIM-33}$, $bla_{VIM-34}$, $bla_{VIM-35}$, $bla_{VIM-39}$, $bla_{VIM-40}$ |
| $bla_{IMP}$ | 43<br>44 | TAGAGTGGCTTAATTCTCRATC<br>CTTCTAWATTTGCGTCACCC | $bla_{IMP-1}$, $bla_{IMP-2}$, $bla_{IMP-4}$, $bla_{IMP-6}$, $bla_{IMP-8}$, $bla_{IMP-10}$, $bla_{IMP-13}$, $bla_{IMP-19}$, $bla_{IMP-24}$, $bla_{IMP-26}$, $bla_{IMP-27}$, $bla_{IMP-32}$, $bla_{IMP-34}$, $bla_{IMP-38}$ |
| $bla_{OXA}$ | 45<br>46 | AGCAAAGGAATGGCAAGAAA<br>CGCCCTGTGATTTATGTTCA | $bla_{OXA-48}$, $bla_{OXA-162}$, $bla_{OXA-163}$, $bla_{OXA-181}$, $bla_{OXA-232}$, $bla_{OXA-244}$, $bla_{OXA-247}$, $bla_{OXA-370}$ |
| $bla_{SHV}$ | 47<br>48 | GGTCAGCGAAAAACAYCTTG<br>GCCTCATTCAGTTCCGTTTC | $bla_{SHV-1}$, $bla_{SHV-2}$, $bla_{SHV-5}$, $bla_{SHV-7}$, $bla_{SHV-8}$, $bla_{SHV-11}$, $bla_{SHV-12}$, $bla_{SHV-13}$, $bla_{SHV-14}$, $bla_{SHV-18}$, $bla_{SHV-24}$, $bla_{SHV-25}$, $bla_{SHV-26}$, $bla_{SHV-27}$, $bla_{SHV-28}$, $bla_{SHV-29}$, $bla_{SHV-30}$, $bla_{SHV-31}$, $bla_{SHV-33}$, $bla_{SHV-36}$, $bla_{SHV-37}$, $bla_{SHV-38}$, $bla_{SHV-40}$, $bla_{SHV-41}$, $bla_{SHV-42}$, $bla_{SHV-44}$, $bla_{SHV-45}$, $bla_{SHV-46}$, $bla_{SHV-49}$, $bla_{SHV-50}$, $bla_{SHV-51}$, $bla_{SHV-52}$, $bla_{SHV-53}$, $bla_{SHV-55}$, $bla_{SHV-56}$, $bla_{SHV-59}$, $bla_{SHV-60}$, $bla_{SHV-61}$, $bla_{SHV-62}$, $bla_{SHV-63}$, |

TABLE 12-continued

Allelic variants with the same primer-binding site.

| Gene | SEQ ID NO | Primer sequence | Detectable allelic variants |
|---|---|---|---|
| | | | bla$_{SHV-64}$, bla$_{SHV-65}$, bla$_{SHV-66}$, bla$_{SHV-67}$, bla$_{SHV-69}$, bla$_{SHV-71}$, bla$_{SHV-72}$, bla$_{SHV-73}$, bla$_{SHV-74}$, bla$_{SHV-76}$, bla$_{SHV-77}$, bla$_{SHV-78}$, bla$_{SHV-79}$, bla$_{SHV-80}$, bla$_{SHV-82}$, bla$_{SHV-83}$, bla$_{SHV-85}$, bla$_{SHV-86}$, bla$_{SHV-92}$, bla$_{SHV-93}$, bla$_{SHV-94}$, bla$_{SHV-95}$, bla$_{SHV-98}$, bla$_{SHV-99}$, bla$_{SHV-101}$, bla$_{SHV-102}$, bla$_{SHV-103}$, bla$_{SHV-104}$, bla$_{SHV-105}$, bla$_{SHV-106}$, bla$_{SHV-107}$, bla$_{SHV-108}$, bla$_{SHV-109}$, bla$_{SHV-110}$, bla$_{SHV-119}$, bla$_{SHV-120}$, bla$_{SHV-121}$, bla$_{SHV-122}$, bla$_{SHV-123}$, bla$_{SHV-124}$, bla$_{SHV-125}$, bla$_{SHV-126}$, bla$_{SHV-128}$, bla$_{SHV-129}$, bla$_{SHV-132}$, bla$_{SHV-133}$, bla$_{SHV-134}$, bla$_{SHV-135}$, bla$_{SHV-137}$, bla$_{SHV-140}$, bla$_{SHV-141}$, bla$_{SHV-142}$, bla$_{SHV-143}$, bla$_{SHV-144}$, bla$_{SHV-145}$, bla$_{SHV-147}$, bla$_{SHV-148}$, bla$_{SHV-149}$, bla$_{SHV-150}$, bla$_{SHV-152}$, bla$_{SHV-153}$, bla$_{SHV-154}$, bla$_{SHV-155}$, bla$_{SHV-156}$, bla$_{SHV-157}$, bla$_{SHV-158}$, bla$_{SHV-159}$, bla$_{SHV-160}$, bla$_{SHV-161}$, bla$_{SHV-162}$, bla$_{SHV-163}$, bla$_{SHV-164}$, bla$_{SHV-165}$, bla$_{SHV-167}$, bla$_{SHV-168}$, bla$_{SHV-172}$, bla$_{SHV-173}$, bla$_{SHV-178}$, bla$_{SHV-179}$, bla$_{SHV-183}$ |
| bla$_{TEM}$ | 49 | GATACGGGAGGGCTTACCAT | bla$_{TEM-1}$, bla$_{TEM-2}$, bla$_{TEM-15}$, bla$_{TEM-17}$, bla$_{TEM-20}$, bla$_{TEM-21}$, bla$_{TEM-22}$, bla$_{TEM-24}$, bla$_{TEM-34}$, bla$_{TEM-40}$, bla$_{TEM-43}$, bla$_{TEM-52}$, bla$_{TEM-53}$, bla$_{TEM-54}$, bla$_{TEM-63}$, bla$_{TEM-70}$, bla$_{TEM-71}$, bla$_{TEM-76}$, bla$_{TEM-78}$, bla$_{TEM-79}$, bla$_{TEM-81}$, bla$_{TEM-82}$, bla$_{TEM-83}$, bla$_{TEM-84}$, bla$_{TEM-88}$, bla$_{TEM-89}$, bla$_{TEM-90}$, bla$_{TEM-95}$, bla$_{TEM-106}$, bla$_{TEM-107}$, bla$_{TEM-109}$, bla$_{TEM-112}$, bla$_{TEM-113}$, bla$_{TEM-114}$, bla$_{TEM-115}$, bla$_{TEM-116}$, bla$_{TEM-120}$, bla$_{TEM-121}$, bla$_{TEM-123}$, bla$_{TEM-124}$, bla$_{TEM-125}$, bla$_{TEM-126}$, bla$_{TEM-131}$, bla$_{TEM-132}$, bla$_{TEM-134}$, bla$_{TEM-135}$, bla$_{TEM-136}$, bla$_{TEM-137}$, bla$_{TEM-142}$, bla$_{TEM-143}$, bla$_{TEM-144}$, bla$_{TEM-149}$, bla$_{TEM-150}$, bla$_{TEM-153}$, bla$_{TEM-154}$, bla$_{TEM-155}$, bla$_{TEM-158}$, bla$_{TEM-159}$, bla$_{TEM-160}$, bla$_{TEM-167}$, bla$_{TEM-169}$, bla$_{TEM-184}$, bla$_{TEM-185}$, bla$_{TEM-195}$, bla$_{TEM-197}$, bla$_{TEM-201}$, bla$_{TEM-207}$, bla$_{TEM-209}$, bla$_{TEM-212}$, bla$_{TEM-216}$, bla$_{TEM-217}$ |
| | 50 | GGATGGAGGCGGATAAAGTT | |
| bla$_{ACC}$ | 51 | GAGCAAATTCGGCAGAGAAA | bla$_{ACC-1}$, bla$_{ACC-4}$, bla$_{ACC-5}$ |
| | 52 | CAAGATGCAACAGGCTCTGA | |

TABLE 13

Confirmed genes encoding different β-lactamases using multiplex real-time PCR.

| DNA Sample | Source | Multiplex real-time PCR |
|---|---|---|
| Salmonella Infantis 50/07 | RKI | TEM |
| Salmonella Typhimurium 58/07 | RKI | SHV |
| Salmonella Infantis 49/07 | RKI | CTX, TEM |
| Salmonella Newport 209/10 | RKI | |
| Salmonella Kentucky 184/10 | RKI | CTX |
| Salmonella Paratyphi 77/08 | RKI | CMY, TEM |
| Salmonella Bareilly 277/10 | RKI | ACC |
| Klebsiella pneumoniae 93/08 | RKI | KPC, SHV, TEM |
| Klebsiella pneumoniae 229/09 | RKI | CTX, OXA-48, TEM, SHV |
| Klebsiella pneumoniae 93/10 | RKI | CTX, CMY, NDM, TEM, SHV |
| Escherichia coli 2/10 | RKI | CTX, NDM, TEM |
| Enterobacter cloacae 146/09 | RKI | VIM, SHV |
| Pseudomonas aeruginosa 82/10 | RKI | IMP |
| Escherichia coli 85.01 | CLS | CTX, TEM |
| Escherichia coli MH01 | CLS | CTX, NDM, TEM |
| Klebsiella pneumoniae KPCG02 | CLS | KPC, SHV, TEM |
| Escherichia coli 14-115-002523 | MU-UH | TEM |
| Escherichia coli 14-139-00319 | MU-UH | CTX |
| Escherichia coli 14-125-002399 | MU-UH | CTX, SHV |
| Escherichia coli 229-1384 | MU-UH | CTX, TEM |
| Enterobacter cloacae 8121 | IMUL | VIM |
| Serratia marcescens 5965 | IMUL | OXA-48 |
| Serratia marcescens 8057 | IMUL | |
| Morganella morganii 7572 | IMUL | NDM |
| Providencia stuartii 8117 | IMUL | VIM, TEM |
| Providencia stuartii 8118 | IMUL | VIM, TEM |
| Pseudomonas aeruginosa 7622 | IMUL | VIM |
| Pseudomonas aeruginosa 6487 | IMUL | VIM |
| Pseudomonas aeruginosa 7072 | IMUL | VIM |
| Klebsiella pneumoniae 7677 | IMUL | VIM, SHV |
| Klebsiella pneumoniae 7678 | IMUL | VIM, SHV |
| Klebsiella pneumoniae 7877 | IMUL | NDM, CTX, TEM, SHV |
| Klebsiella pneumoniae 7932 | IMUL | NDM, CTX, SHV |
| Klebsiella pneumoniae 8052 | IMUL | KPC, TEM, SHV |
| Klebsiella pneumoniae 8083 | IMUL | KPC, TEM, SHV |
| Klebsiella pneumoniae 8161 | IMUL | KPC, TEM, SHV |
| Escherichia coli 7469 | IMUL | OXA-48, TEM |
| Enterobacter cloacae 8088 | IMUL | OXA-48 |
| Proteus mirabilis 111554 | bioMérieux | CMY, TEM |
| Klebsiella pneumoniae 110220 | bioMérieux | ACC, TEM, SHV |
| Escherichia coli 104039 | bioMérieux | TEM |
| Escherichia coli 111564 | bioMérieux | VIM, CMY |
| Pseudomonas aeruginosa 111615 | bioMérieux | IMP |
| Klebsiella pneumoniae 111622 | bioMérieux | KPC, TEM, SHV |
| Escherichia coli 109423 | bioMérieux | SHV |
| Klebsiella pneumoniae 115415 | bioMérieux | KPC, TEM, SHV |
| Klebsiella pneumoniae 113260 | bioMérieux | OXA, TEM, SHV |
| Escherichia coli 115434 | bioMérieux | CTX, CMY |
| Escherichia coli JJ1886 | VAMC | CTX |
| Escherichia coli JJ2468 | VAMC | CTX |
| Escherichia coli JJ2625 | VAMC | CTX |
| Escherichia coli JJ2227 | VAMC | |
| Escherichia coli JJ2060 | VAMC | |
| Escherichia coli JJ2084 | VAMC | |

TABLE 13-continued

Confirmed genes encoding different β-lactamases using multiplex real-time PCR.

| DNA Sample | Source | Multiplex real-time PCR |
|---|---|---|
| Escherichia coli JJ2482 | VAMC | |
| Escherichia coli JJ2226 | VAMC | CTX |

Abbreviations:

Robert Koch Institute (RKI), Berlin, Germany; Calgary Laboratory Services (CLS), Calgary, AB, Canada; University Hospital, University of Missouri (MU-UH), Columbia, Mo., USA; Institute of Microbiology, University of Lausanne and University Hospital Center (IMUL), Lausanne, Switzerland; bioMérieux, St. Louis, Mo., USA; Minneapolis VA Health Care System (VAMC), Minneapolis, Minn., USA.

Example 4

High-Resolution Melt Assay for Specific Identification of E. coli O157

E. coli O157 uidA gene+93 mutation is the most commonly used target for the identification of E. coli O157 serogroup. In this study, a high-resolution melting assay (HRMA) was designed for the identification of uidA gene+93 mutation. The assay was validated using 120 strains of E. coli and Shigella.

Melt curve analysis of amplicons generated in a qPCR reaction using high-resolution dyes is known as high-resolution melting curve analysis (HRMA). The advantage of HRMA qPCR assay, its ease of use, high sensitivity, low cost and non-destructive nature makes this a tool of choice in the field of SNP genotyping. Owing to its simplicity and ease of use its application in the areas of clinical diagnostics and food safety has also increased. The aim of this study was to develop a HRMA for the identification of E. coli O157 serogroup.

Bacterial Strains:

E. coli O157 and non-O157 STEC strains were procured from the STEC Center at Michigan State University (Michigan, USA) (Table 14). E. coli, E. coli O157 and Shigella strains were obtained from the University of Missouri, Food Microbiology Lab culture collection. Cultures were grown at 37° C. in Tryptic Soy broth (TSB) (Difco Labs., MD, USA).

Bacterial DNA Extraction:

Genomic DNA from all bacterial strains used in the study was isolated using PrepMan® Ultra Sample Preparation Reagent (Applied Biosystems, Foster City, Calif., USA) according to the manufacturer's instructions. The concentrations and purity of the obtained DNA samples was measured using NanoDrop™ Lite Spectrophotometer (Thermo Fisher Scientific, Wilmington, Del., USA).

Primer Design:

The primer pairs, HRM-F: GCCCGGCTTTCTTGTAAC (SEQ ID NO:54) and HRM-R1: GATCGCGAAAACTGTGGAAT (SEQ ID NO:55) amplifying the +93 uidA mutation of E. coli O157, was designed using the Primer3 software. The specificity of the designed PCR primers was tested using the NCBI/Primer-BLAST. The oligonucleotides were commercially synthesized (IDT, Coraville, Iowa, USA).

Real-Time PCR:

Real-time PCR assay was performed using 2× LightCycler® 480 High Resolution Melting Master (Roche Diagnostics Corp., Indianapolis, USA). The HRM assay was standardized on a LightCycler® 96 real-time PCR (Roche Diagnostics Corp., Indianapolis, USA). PCR was performed with a 10 μL reaction volume in duplicate, with 30 ng of genomic DNA, 0.5 μM primers and 2.5 mM $MgCl_2$. A two-step amplification protocol included an initial denaturation at 94° C. for 10 min, followed by 40 cycles of 95° C. for 15 s, and 64° C. for 30 s. A high-resolution melt curve step was added at the end of the PCR amplification (from 60° C. to 95° C., with gradual temperature increments of 0.04° C./s). A high-resolution melt curve analysis was performed with the pre-melt region of 76.9-77.9° C. and post-melt region of 87.7-88.7° C.

Results:

High-resolution melt assay for the differentiation of E. coli O157 from other E. coli strain was initially standardized using pure DNA samples. Magnesium chloride ($MgCl_2$) concentration in the PCR reaction mix is one of the most important factors for the clear differentiation of genotypes by HRMA. The HRM assay was performed with different $MgCl_2$ concentrations and 2.5 mM $MgCl_2$ was found to be optimum for the assay. The optimized assay was validated using a set of 120 bacterial strains comprised of 12 E. coli O157, 9 E. coli O26, 10 E. coli O45, 10 E. coli O103, 6 E. coli O104, 10 E. coli O111, 10 E. coli O121, 9 E. coli O145, 3 Shigella, and 40 E. coli strains isolated from the feces of eight different animals (chicken, cattle, duck, dog, goose, goat, human, pig) (Table 14). Equal concentration mixtures of E. coli O157 and E. coli DNA were used to create a heterozygous genotype (mix). The HRM assay was able to clearly discriminate E. coli O157 strains from other E. coli and Shigella (FIG. 7A).

TABLE 14

Escherichia coli and Shigella strains used in this study.

| O-Serogroup | Strains | Source |
|---|---|---|
| E. coli O157 | 93-111 | Human (USA) |
| E. coli O157 | EDL-933 | Food (hamburger) |
| E. coli O157 | OK-1 | Human (Japan) |
| E. coli O157 | 2886-75 | Human (USA) |
| E. coli O157 | 86-24 | Human (USA) |
| E. coli O157 | G5101 | Human (USA) |
| E. coli O157 | ATCC 43894 | Human (USA) |
| E. coli O157:H7 | 505B | Beef (FRI) |
| E. coli O157:H7 | 3178-85 | Human (CDC) |
| E. coli O157:H7 | 43894 | Human |
| E. coli O157:H7 | C7927 | Human (CDC) |
| E. coli O157:H7 | MF 1847 | Beef (FSIS) |
| E. coli O26 | DEC10C | Human Infant USA |
| E. coli O26 | DEC9F | Human (USA) |
| E. coli O26 | TB285C | Human (USA) |
| E. coli O26 | VP30 | Human (Chile) |
| E. coli O26 | DEC9A | Human (USA) |
| E. coli O26:H11 | DEC10B | Human (Australia) |
| E. coli O26:H11 | 97-3250 | Human (USA) |
| E. coli O26:H | MT#10 | Human (USA) |
| E. coli O26:H N | TB352A | Human (USA) |
| E. coli O45 | DEC11C | Human (USA) |
| E. coli O45 | 5431-72 | Human (Canada) |
| E. coli O45 | 4309-65 | Human (USA) |
| E. coli O45 | 88-4110-H | Cow (USA) |
| E. coli O45 | D88-28058 | Cow (USA) |
| E. coli O45 | 2566-58 | Pig (UK) |
| E. coli O45:H2 | M103-19 | Human (USA) |
| E. coli O45:H2 | MI01-88 | Human (USA) |
| E. coli O45:H2 | MI05-14 | Human (USA) |
| E. coli O45:H NM | DA-21 | Human (USA) |

TABLE 14-continued

*Escherichia coli* and *Shigella* strains used in this study.

| O-Serogroup | Strains | Source |
|---|---|---|
| E. coli O103:H2 | MT#80 | Human (USA) |
| E. coli O103:H6 | TB154A | Human (USA) |
| E. coli O103:H25 | 8419 | Human (USA) |
| E. coli O103:H N | PT91-24 | Human (USA) |
| E. coli O103 | DA-41 | Human (USA) |
| E. coli O103 | 6:38 | Human (USA) |
| E. coli O103 | PT91-24 | Human (USA) |
| E. coli O103 | DA-55 | Human (USA) |
| E. coli O103 | 87-2931 | Human (Canada) |
| E. coli O103 | GS G5550637 | Human (USA) |
| E. coli O104:H | ECOR-28 | Human (USA) |
| E. coli O104:H | G5506 | Human (USA) |
| E. coli O104:H | G5508 | Human (USA) |
| E. coli O104:H | TW01435 | Cow (Germany) |
| E. coli O104 | O104 standard | |
| E. coli O104 | E28 | Human (USA) |
| E. coli O111 | CL-37 | Human (Canada) |
| E. coli O111 | DEC8B | Human (USA) |
| E. coli O111 | TB226A | Human (USA) |
| E. coli O111 | 928/91 | Human (Germany) |
| E. coli O111 | 412/55 | Human (Germany) |
| E. coli O111 | DEC8C | Cow (USA) |
| E. coli O111.H2 | RD8 | Human (France) |
| E. coli O111:H8 | 3215-99 | Human (USA) |
| E. coli O111:H11 | 0201 9611 | Human (USA) |
| E. coli O111:H NM | 3007-85 | Human (USA) |
| E. coli O121:H19 | 3377-85 | Human (USA) |
| E. coli O121:H19 | MT#2 | Human (USA) |
| E. coli O121:H | MT#18 | Human (USA) |
| E. coli O121:H[19] | DA-5 | Human (USA) |
| E. coli O121 | 87-2914 | Human (Canada) |
| E. coli O121 | DA-1 | Human (USA) |
| E. coli O121 | 7927+++ | |
| E. coli O121 | 5518 | |
| E. coli O121 | O121 standard | |
| E. coli O121 | PT91-4 | |
| E. coli O145 | 70300885 | |
| E. coli O145 | MT#66 | Human (USA) |
| E. coli O145 | 6940 | |
| E. coli O145 | TB269C | Human (USA) |
| E. coli O145 | DEC10I | Human (Canada) |
| E. coli O145:H NT | D177 | |
| E. coli O145:H[28] | 4865/96 | Human (Germany) |
| E. coli O145:H NM | GS G5578620 | Human (USA) |
| E. coli O145:H NT | IH 16 | Human (Uruguay) |
| S. dysenteriae | ATCC 29028 | |
| S. flexneri | | |
| S. sonnei | | |
| E. coli | C1 | Chicken |
| E. coli | C2 | Chicken |
| E. coli | C3 | Chicken |
| E. coli | C4 | Chicken |
| E. coli | C5 | Chicken |
| E. coli | Ct1 | Cattle |
| E. coli | Ct2 | Cattle |
| E. coli | Ct3 | Cattle |
| E. coli | Ct4 | Cattle |
| E. coli | Ct5 | Cattle |
| E. coli | D1 | Duck |
| E. coli | D3 | Duck |
| E. coli | D4 | Duck |
| E. coli | D5 | Duck |
| E. coli | D6 | Duck |
| E. coli | Dg2 | Dog |
| E. coli | Dg3 | Dog |
| E. coli | Dg4 | Dog |
| E. coli | Dg5 | Dog |
| E. coli | Dg6 | Dog |
| E. coli | G2 | Goose |
| E. coli | G4 | Goose |
| E. coli | G5 | Goose |
| E. coli | G8 | Goose |
| E. coli | G9 | Goose |
| E. coli | Gt2 | Goat |
| E. coli | Gt3 | Goat |
| E. coli | Gt4 | Goat |
| E. coli | Gt5 | Goat |
| E. coli | Gt6 | Goat |
| E. coli | H2 | Human |
| E. coli | H3 | Human |
| E. coli | H10 | Human |
| E. coli | H11 | Human |
| E. coli | H12 | Human |
| E. coli | P10 | Pig |
| E. coli | P17 | Pig |
| E. coli | P22 | Pig |
| E. coli | P23 | Pig |
| E. coli | P24 | Pig |

Based on the +93 uidA gene mutation found in *E. coli* O157, Cebula et al. (*J Clin Microbiol* 33:248-250, 1995) designed a mismatch amplification mutation assay (MAMA) for the detection of *E. coli* O157. It is one of the most commonly used methods for the identification of *E. coli* O157. However, under relaxed PCR conditions, the assay can also amplify the uidA gene of other *E. coli* or *Shigella*, generating a false positive result. Hence, the HRMA assay developed in this study was further validated using *Shigella* strains. The melt profile generated by the *Shigella* uidA gene amplicon grouped with other *E. coli*, proving the specificity of the assay towards only the *E. coli* O157 serogroup.

Out of 40 *E. coli* strains isolated from the feces of 8 different animals, the melt curve profile of 38 strains aligned with one another, but two strains (Dg2 and H2) generated a separate profile in the differential plot (FIG. 7B). The plot generated by these two strains was different from the plots obtained from *E. coli* O157 and other *E. coli* tested in this study. Formation of a separate melt curve profile in the differential plot indicates the presence of some other mutations in the amplicon region of the targeted uidA gene sequences. A GenBank nucleotide data search on the *Shigella* uidA gene revealed the presence of two single nucleotide polymorphisms (SNP) in the amplicon region. Due to the high sensitivity of the HRMA, the presence of any other SNP is expected to form a separate melt profile (other than *E. coli* O157) on the differential plot.

Hence it can be concluded that HRMA for the detection of *E. coli* O157 developed in this study is a simple, low cost, nondestructive technique, which offers genotyping and allelic differentiation with high sensitivity and specificity.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for detection of at least one bacterial species in a biological sample comprising real-time PCR amplification, said method comprising:
   (i) enriching the bacterial concentration of the biological sample to result in an enriched biological sample;
   (ii) isolating DNA from said enriched biological sample to produce an isolated DNA sample; and
   (iii) detecting a sequence from said at least one bacterial species in said isolated DNA sample via real-time PCR, wherein said real-time PCR comprises:
   (a) an internal amplification control comprising at least 90% identity to the internal amplification control set forth in SEQ ID NO:23 and more than one primer pair, wherein each primer of the primer pairs comprises at least 90% sequence identity to a primer set forth in SEQ ID NO:1, SEQ ID NO:2, SEQ ID NO:3, SEQ ID NO:4, SEQ ID NO:7, SEQ ID NO:8, SEQ ID NO:19, SEQ ID NO:20, SEQ ID NO:21 or SEQ ID NO:22;
   (b) an internal amplification control comprising at least 90% identity to the internal amplification control set forth in SEQ ID NO:31 and more than one primer pair, wherein each primer of the primer pairs comprises at least 90% sequence identity to a primer set forth in SEQ ID NO:24, SEQ ID NO:25, SEQ ID NO:26, SEQ ID NO:27, SEQ ID NO:14, SEQ ID NO:15, SEQ ID NO:16, SEQ ID NO:28, SEQ ID NO:29 or SEQ ID NO:30;
   (c) an internal amplification control comprising at least 90% identity to the internal amplification control set forth in SEQ ID NO:42 and more than one primer pair, wherein each primer of the primer pairs comprises at least 90% sequence identity to a primer set forth in SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 or SEQ ID NO:41; or
   (d) an internal amplification control comprising at least 90% identity to the internal amplification control set forth in SEQ ID NO:53 and more than one primer pair, wherein each primer of the primer pairs comprises at least 90% sequence identity to a primer set forth in SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51 or SEQ ID NO:52.

2. The method of claim 1, wherein said real-time PCR comprises an internal amplification control comprising at least 90% identity to the internal amplification control set forth in SEQ ID NO:23 and more than one primer pair, wherein each primer of the primer pairs comprises at least 90% sequence identity to a primer set forth in SEQ ID NO:1, SEQ ID NO:2, SEQ ID NO:3, SEQ ID NO:4, SEQ ID NO:7, SEQ ID NO:8, SEQ ID NO:19, SEQ ID NO:20, SEQ ID NO:21 or SEQ ID NO:22.

3. The method of claim 1, wherein said real-time PCR comprises an internal amplification control comprising at least 90% identity to the internal amplification control set forth in SEQ ID NO:31 and more than one primer pair, wherein each primer of the primer pairs comprises at least 90% sequence identity to a primer set forth in SEQ ID NO:24, SEQ ID NO:25, SEQ ID NO:26, SEQ ID NO:27, SEQ ID NO:14, SEQ ID NO:15, SEQ ID NO:16, SEQ ID NO:28, SEQ ID NO:29 or SEQ ID NO:30.

4. The method of claim 1, wherein said real-time PCR comprises an internal amplification control comprising at least 90% identity to the internal amplification control set forth in SEQ ID NO:42 and more than one primer pair, wherein each primer of the primer pairs comprises at least 90% sequence identity to a primer set forth in SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 or SEQ ID NO:41.

5. The method of claim 1, wherein said real-time PCR comprises an internal amplification control comprising at least 90% identity to the internal amplification control set forth in SEQ ID NO:53 and more than one primer pair, wherein each primer of the primer pairs comprises at least 90% sequence identity to a primer set forth in SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51 or SEQ ID NO:52.

6. The method of claim 1, wherein said real-time PCR comprises:
(a) the internal amplification control set forth in SEQ ID NO:23 and more than one primer pair selected from: (i) SEQ ID NO:1 and SEQ ID NO:2, (ii) SEQ ID NO:3 and SEQ ID NO:4, (ii) SEQ ID NO:7 and SEQ ID NO:8, (iv) SEQ ID NO:19 and SEQ ID NO:20, and (v) SEQ ID NO:21 and SEQ ID NO:22;
(b) the internal amplification control set forth in SEQ ID NO:31 and more than one primer pair selected from: (i) SEQ ID NO:24 and SEQ ID NO:25, (ii) SEQ ID NO:26 and SEQ ID NO:27, (iii) SEQ ID NO:14 and SEQ ID NO:15, (iv) SEQ ID NO:16 and SEQ ID NO:28, and (v) SEQ ID NO:29 and SEQ ID NO:30;
(c) the internal amplification control set forth in SEQ ID NO:42 and more than one primer pair selected from: (i) SEQ ID NO:32 and SEQ ID NO:33, (ii) SEQ ID NO:34 and SEQ ID NO:35, (iii) SEQ ID NO:36 and SEQ ID NO:37, (iv) SEQ ID NO:38 and SEQ ID NO:39, and (v) SEQ ID NO:40 and SEQ ID NO:41; or
(d) the internal amplification control set forth in SEQ ID NO:53 and more than one primer pair selected from: (i) SEQ ID NO:43 and SEQ ID NO:44, (ii) SEQ ID NO:45 and SEQ ID NO:46, (iii) SEQ ID NO:47 and SEQ ID NO:48, (iv) SEQ ID NO:49 and SEQ ID NO-50, and (v) SEQ ID NO:51 and SEQ ID NO:52.

7. The method of claim 6, wherein said real-time PCR comprises the internal amplification control set forth in SEQ ID NO:23 and more than one primer pair selected from: (i) SEQ ID NO:1 and SEQ ID NO:2, (ii) SEQ ID NO:3 and SEQ ID NO:4, (iii) SEQ ID NO:7 and SEQ ID NO:8, (iv) SEQ ID NO:19 and SEQ ID NO:20, and (v) SEQ ID NO:21 and SEQ ID NO:22.

8. The method of claim 6, wherein said real-time PCR comprises the internal amplification control set forth in SEQ ID NO:31 and more than one primer pair selected from: (i) SEQ ID NO:24 and SEQ ID NO:25, (ii) SEQ ID NO:26 and SEQ ID NO:27, (iii) SEQ ID NO:14 and SEQ ID NO:15, (iv) SEQ ID NO:16 and SEQ ID NO:28, and (v) SEQ ID NO:29 and SEQ ID NO:30.

9. The method of claim 6, wherein said real-time PCR comprises the internal amplification control set forth in SEQ ID NO:42 and more than one primer pair selected from: (i) SEQ ID NO:32 and SEQ ID NO:33, (ii) SEQ ID NO:34 and SEQ ID NO:35, (iii) SEQ ID NO:36 and SEQ ID NO:37, (iv) SEQ ID NO:38 and SEQ ID NO:39, and (v) SEQ ID NO:40 and SEQ ID NO:41.

10. The method of claim 6, wherein said real-time PCR comprises the internal amplification control set forth in SEQ ID NO:53 and more than one primer pair selected from: (i) SEQ ID NO:43 and SEQ ID NO:44, (ii) SEQ ID NO:45 and SEQ ID NO:46, (iii) SEQ ID NO:47 and SEQ ID NO:48, (iv) SEQ ID NO:49 and SEQ ID NO:50, and (v) SEQ ID NO:51 and SEQ ID NO:52.

11. The method of claim 1, wherein said method further comprises a melt curve assay for visualization of individual amplicons.

12. The method of claim 11, wherein said melt curve assay uses real-time PCR with SEQ ID NO: 54 and SEQ ID NO: 55.

13. The method of claim 1, wherein detecting said at least one sequence comprises:
(1) a first real-time PCR with the more than one primer pair and the internal amplification control of part (a) and a second real-time PCR with the more than one primer pair and the internal amplification control of part (b); or
(2) a first real-time PCR with the more than one primer pair and the internal amplification control of part (c) and a second real-time PCR with the more than one primer pair and the internal amplification control of part (d).

14. The method of claim 1, wherein said enriching step comprises incubating said biological sample aerobically at approximately 42° C. in an enrichment media.

15. The method of claim 14, wherein said enrichment media is selected from the group consisting of brain heart infusion broth (BHI), tryptic soy broth (TSB), and Buffered Peptone Water (BPW).

16. The method of claim 15, wherein said enrichment media is supplemented with an antibiotic.

17. The method of claim 16, wherein said enrichment media is BPW supplemented with vancomycin.

18. The method of claim 1, wherein said biological sample comprises a food or a beverage.

19. The method of claim 18, wherein said food or beverage comprises meat, produce, or juice.

20. The method of claim 1, wherein said biological sample comprises a clinical sample.

21. The method of claim 20, wherein said clinical sample comprises stool, urine, or blood.

22. The method of claim 1, wherein said sequence comprises:
(1) a sequence from at least one bacterial species selected from the group consisting of *E. coli* O121, *E. coli* O145, *E. coli* O157, *E. coli* O26, *E. coli* O111, *E. coli* O103, *E. coli* O45, and *Salmonella*; or a $stx_1$ or $stx_2$ sequence; or
(2) a sequence selected from the group consisting of $bla_{KPC-like}$, $bla_{NDM-like}$, $bla_{CTX-M-1/2group}$, $bla_{CMY-like}$, $bla_{VIM-like}$, $bla_{IMP-like}$, $bla_{OXA-like}$, $bla_{SHV-like}$, $bla_{TEM-like}$, and $bla_{ACC-like}$.

23. A kit for detection of at least one bacterial species in a biological sample, comprising:
- (i) an internal amplification control comprising at least 90% identity to the internal amplification control set forth in SEQ ID NO:23 and more than one primer pair, wherein each primer of the primer pairs comprises at least 90% sequence identity to a primer set forth in SEQ ID NO:1, SEQ ID NO:2, SEQ ID NO:3, SEQ ID NO:4, SEQ ID NO:7, SEQ ID NO:8, SEQ ID NO:19, SEQ ID NO:20, SEQ ID NO:21 or SEQ ID NO:22;
- (ii) an internal amplification control comprising at least 90% identity to the internal amplification control set forth in SEQ ID NO:31 and more than one primer pair, wherein each primer of the primer pairs comprises at least 90% sequence identity to a primer set forth in SEQ ID NO:24, SEQ ID NO:25, SEQ ID NO:26, SEQ ID NO:27, SEQ ID NO:14, SEQ ID NO:15, SEQ ID NO:16, SEQ ID NO:28, SEQ ID NO:29 or SEQ ID NO:30;
- (iii) an internal amplification control comprising at least 90% identity to the internal amplification control set forth in SEQ ID NO:42 and more than one primer pair, wherein each primer of the primer pairs comprises at least 90% sequence identity to a primer set forth in SEQ ID NO:32, SEQ ID NO:33, SEQ ID NO:34, SEQ ID NO: 35, SEQ ID NO:36, SEQ ID NO:37, SEQ ID NO:38, SEQ ID NO: NO:39, SEQ ID NO:40 or SEQ ID NO:41; or
- (iv) an internal amplification control comprising at least 90% identity to the internal amplification control set forth in SEQ ID NO:53 and more than one primer pair, wherein each primer of the primer pairs comprises at least 90% sequence identity to a primer set forth in SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51 or SEQ ID NO:52.

24. The kit of claim 23, further comprising a primer pair of SEQ ID NO: 54 and SEQ ID NO: 55.

25. The kit of claim 23, comprising an internal amplification control comprising at least 90% identity to the internal amplification control set forth in SEQ ID NO:23 and more than one primer pair, wherein each primer of the primer pairs comprises at least 90% sequence identity to a primer set forth in SEQ ID NO:1, SEQ ID NO:2, SEQ ID NO:3, SEQ ID NO:4, SEQ ID NO:7, SEQ ID NO:8, SEQ ID NO:19, SEQ ID NO:20, SEQ ID NO:21, or SEQ ID NO:22.

26. The kit of claim 23, comprising an internal amplification control comprising at least 90% identity to the internal amplification control set form in SEQ ID NO:31 and more than one primer pair, wherein each primer of the primer pairs comprises at least 90% sequence identity to a primer set forth in SEQ ID NO:24, SEQ ID NO:25, SEQ ID NO:26, SEQ ID NO:27, SEQ ID NO:14, SEQ ID NO:15, SEQ ID NO:16, SEQ ID NO:28, SEQ ID NO:29, or SEQ ID NO:30.

27. The kit of claim 23, comprising an internal amplification control comprising at least 90% identity to the internal amplification control set forth in SEQ ID NO:42 and more than one primer pair, wherein each primer of the primer pairs comprises at least 90% sequence identity to a primer set forth in SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41.

28. The kit of claim 23, comprising an internal amplification control comprising at least 90% identity to the internal amplification control set forth in SEQ ID NO:53 and more than one primer pair, wherein each primer of the primer pairs comprises at least 90% sequence identity to a primer set forth in SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52.

* * * * *

SEQUENCE LISTING

<160> NUMBER OF SEQ ID NOS: 55

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
actgggattg gacgtggata                                                      20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tcctcccaaa acttctaggc                                                      20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tggctagtgg cattctgatg                                                      20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
atgcgcttac tcccaagatg                                                      20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ccgtaattga aaagcttggt g                                                    21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cggctgcaag tatcctaagc                                                      20

<210> SEQ ID NO 7
<211> LENGTH: 21
<212> TYPE: DNA
<213> ORGANISM: Artificial Sequence -continued

```
<220> FEATURE:
<223> OTHER INFORMATION: Primer

<400> SEQUENCE: 7
ttgacccaca ctttgccgta a                                             21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gcgaaaactg tggaattggg                                               20

<210> SEQ ID NO 9
<211> LENGTH: 149
<212> TYPE: DNA
<213> ORGANISM: Artificial Sequence
<220> FEATURE:
<223> OTHER INFORMATION: Artificial Internal Amplification Control

<400> SEQUENCE: 9
tggctagtgg cattctgatg catggtggca tggggatttt ttgctgcaag tgggctgtcc   60
agacagttca tagttggttt ggccatatct gtcgcattac gagaaacttt catcgttggt  120
ttaacatggc atcttgggag taagcgcat                                    149

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tctggcgtgc tatcgcttat                                               20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ttccgcccat tgaattttag                                               20

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gtctggctgc agggacttt                                                19

<210> SEQ ID NO 13
<211> LENGTH: 20
<212> TYPE: DNA
<213> ORGANISM: Artificial Sequence
<220> FEATURE:
<223> OTHER INFORMATION: Primer
```

```
<400> SEQUENCE: 13
agacgagcct ggctttgata                                               20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tagaggatgc cggatattgg                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gcgagcggta caacaataca                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aaggcgaggc aacacattat                                               20

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
cgatgttgat catctgggag a                                             21

<210> SEQ ID NO 18
<211> LENGTH: 154
<212> TYPE: DNA
<213> ORGANISM: Artificial Sequence
<220> FEATURE:
<223> OTHER INFORMATION: Artificial Internal Amplification Control

<400> SEQUENCE: 18
aaggcgaggc aacacattat tgaccctgcg ctctacccga tagctgaggc ggactgcagg    60
ctggtggtag cactcagcgc agcgggatgg catcgccacc cgcaccggtc acctcgaccc   120
gagacgcgct cgatctccca gatgatcaac atcg                              154

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
taccactctg caacgtgtcg                                               20
```

```
<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
aggcttctgc tgtgacagtg                                             20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
atcgctttrc tgatttttca                                             20

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
caatgtaacc gcwsttgtac c                                           21

<210> SEQ ID NO 23
<211> LENGTH: 83
<212> TYPE: DNA
<213> ORGANISM: Artificial Sequence
<220> FEATURE:
<223> OTHER INFORMATION: Artificial Internal Amplification Control

<400> SEQUENCE: 23
catatatggc tagtggcatt ctgatgatat atatattatc aaaataagac taataaagca   60
tcttgggagt aagcgcatca tac                                          83

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
aagcgcgttc atccctttat                                             20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
acaatccaac cgaaccaaac                                             20

<210> SEQ ID NO 26
<211> LENGTH: 19
<212> TYPE: DNA
```

```
<213> ORGANISM: Artificial Sequence
<220> FEATURE:
<223> OTHER INFORMATION: Primer

<400> SEQUENCE: 26
ggactttcgt tgcgttgtg                                                      19

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
gcctggcttt gataccatgt                                                     20

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
gccaaaggta ttcacgatgt t                                                   21

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cggtgggttt tgttgtcttc                                                     20

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
tcatcgcacc gtcaaagga                                                      19

<210> SEQ ID NO 31
<211> LENGTH: 83
<212> TYPE: DNA
<213> ORGANISM: Artificial Sequence
<220> FEATURE:
<223> OTHER INFORMATION: Artificial Internal Amplification Control

<400> SEQUENCE: 31
catatataga ggatgccgga tattggatat atatattatc aaaataagac taataaagtg         60
tattgttgta ccgctcgcca tac                                                 83

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
```
gtcggagaca aaaccggaac                                           20

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
atagtcattt gccgtgccat a                                         21

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
tggatcaagc aggagatcaa                                           20

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
ggccggggta aataccctt                                            19

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
aatctgacgc tgggtaaag                                            19

<210> SEQ ID NO 37
<211> LENGTH: 17
<212> TYPE: DNA
<213> ORGANISM: Artificial Sequence
<220> FEATURE:
<223> OTHER INFORMATION: Primer

<400> SEQUENCE: 37
ccgctgccgg ttttatc                                              17

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gttcaggaga aaacgctcca                                           20

<210> SEQ ID NO 39
<211> LENGTH: 20
<212> TYPE: DNA

```
<213> ORGANISM: Artificial Sequence
<220> FEATURE:
<223> OTHER INFORMATION: Primer

<400> SEQUENCE: 39
ccagcctaat ccctggtaca                                                 20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
tcattgtccg tgatggtgat                                                 20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
caccccacgc tgtatcaatc                                                 20

<210> SEQ ID NO 42
<211> LENGTH: 82
<212> TYPE: DNA
<213> ORGANISM: Artificial Sequence
<220> FEATURE:
<223> OTHER INFORMATION: Artificial Internal Amplification Control

<400> SEQUENCE: 42
catatatgga tcaagcagga gatcaaatat atatattatc aaaataagac taataaagaa     60
ggtattttac cccggcccat ac                                              82

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
tagagtggct taattctcra tc                                              22

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
cttctawatt tgcgtcaccc                                                 20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
```

-continued agcaaaggaa tggcaagaaa                                                   20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
cgccctgtga tttatgttca                                                   20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
ggtcagcgaa aacaycttg                                                    20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
gcctcattca gttccgtttc                                                   20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
gatacgggag ggcttaccat                                                   20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
ggatggaggc ggataaagtt                                                   20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
gagcaaattc ggcagagaaa                                                   20

<210> SEQ ID NO 52
<211> LENGTH: 20
<212> TYPE: DNA

```
<213> ORGANISM: Artificial Sequence
<220> FEATURE:
<223> OTHER INFORMATION: Primer

<400> SEQUENCE: 52
caagatgcaa caggctctga                                              20

<210> SEQ ID NO 53
<211> LENGTH: 83
<212> TYPE: DNA
<213> ORGANISM: Artificial Sequence
<220> FEATURE:
<223> OTHER INFORMATION: Artificial Internal Amplification Control

<400> SEQUENCE: 53
catataggtc agcgaaaaac aycttgatat atatattatc aaaataagac taataaagga   60
aacggaactg aatgaggcca tac                                          83

<210> SEQ ID NO 54
<211> LENGTH: 18
<212> TYPE: DNA
<213> ORGANISM: Artificial Sequence
<220> FEATURE:
<223> OTHER INFORMATION: Primer

<400> SEQUENCE: 54
gcccggcttt cttgtaac                                                18

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gatcgcgaaa actgtggaat                                              20
```